(12) United States Patent
Mabry et al.

(10) Patent No.: US 7,968,585 B2
(45) Date of Patent: Jun. 28, 2011

(54) INHIBITORS OF 11-BETA-HYDROXYSTEROID DEHYDROGENASE 1

(75) Inventors: Thomas Edward Mabry, Indianapolis, IN (US); Owen Brendan Wallace, Westfield, IN (US); Yanping Xu, Noblesville, IN (US); Nancy June Snyder, Lizton, IN (US); Leonard Larry Winneroski, Jr., Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 128 days.

(21) Appl. No.: 12/297,906

(22) PCT Filed: Apr. 25, 2007

(86) PCT No.: PCT/US2007/067350
§ 371 (c)(1),
(2), (4) Date: Oct. 21, 2008

(87) PCT Pub. No.: WO2007/127763
PCT Pub. Date: Nov. 8, 2007

(65) Prior Publication Data
US 2009/0099180 A1   Apr. 16, 2009

Related U.S. Application Data

(60) Provisional application No. 60/745,574, filed on Apr. 25, 2006.

(51) Int. Cl.
*A01N 43/38* (2006.01)
*A01N 43/36* (2006.01)
*A61K 31/40* (2006.01)
*C07D 209/54* (2006.01)
*C07D 209/96* (2006.01)
*C07D 207/00* (2006.01)

(52) U.S. Cl. ......... 514/409; 514/424; 548/408; 548/543

(58) Field of Classification Search .................. 514/409, 514/424; 548/408, 543
See application file for complete search history.

(56) References Cited

U.S. PATENT DOCUMENTS

| | | | |
|---|---|---|---|
| 7,713,979 B2 * | 5/2010 | Aicher et al. | ............ 514/254.02 |
| 2008/0207691 A1 | 8/2008 | Aicher et al. | |
| 2008/0214621 A1 | 9/2008 | Aicher et al. | |
| 2008/0275043 A1 | 11/2008 | Aicher et al. | |
| 2009/0069326 A1 | 3/2009 | Allen et al. | |
| 2009/0088428 A1 | 4/2009 | Saeed et al. | |
| 2009/0088430 A1 | 4/2009 | Wallace et al. | |
| 2009/0099182 A1 | 4/2009 | Li et al. | |
| 2009/0111800 A1 | 4/2009 | Aicher et al. | |
| 2009/0111809 A1 | 4/2009 | Bush et al. | |
| 2009/0156571 A1 | 6/2009 | Aicher et al. | |
| 2009/0239911 A1 | 9/2009 | Wallace et al. | |
| 2009/0264650 A1 | 10/2009 | Toshiro et al. | |
| 2009/0275613 A1 | 11/2009 | Li et al. | |

FOREIGN PATENT DOCUMENTS

| | | |
|---|---|---|
| EP | 1864971 | 12/2007 |
| WO | WO 2004/056744 | 7/2004 |
| WO | WO 2005/108360 | 11/2005 |
| WO | WO 2005/108361 | 11/2005 |
| WO | WO 2006/040329 | 4/2006 |
| WO | WO 2006/049952 | 5/2006 |
| WO | WO 2006/053024 | 5/2006 |
| WO | WO 2006/068991 | 6/2006 |
| WO | WO 2006/068992 | 6/2006 |
| WO | WO 2006/104280 | 10/2006 |
| WO | WO 2007/084314 | 7/2007 |
| WO | WO 2007/124254 | 11/2007 |
| WO | WO 2007/124329 | 11/2007 |
| WO | WO 2007/124337 | 11/2007 |
| WO | WO 2007/127688 | 11/2007 |
| WO | WO 2007/127693 | 11/2007 |
| WO | WO 2007/127704 | 11/2007 |
| WO | WO 2007/127726 | 11/2007 |

(Continued)

OTHER PUBLICATIONS

Obniska J, Kaminski K, Zagorska A, Dzierzawska-Majewska A, and Karolak-Wojciechowska J, "Synthesis and anticonvulsant activity of new fluorinated N-phenyl- and N-benzyl-2-azaspiro[4.4]nonane- and [4.5]decane-1,3-dione derivatives: Part III," Journal of Fluorine Chemistry, Mar. 2006, 127(3), 417-425 (available online Feb. 23, 2006).*

(Continued)

*Primary Examiner* — San-ming Hui
*Assistant Examiner* — Paul Zarek
(74) *Attorney, Agent, or Firm* — Dan L. Wood

(57) ABSTRACT

The present invention discloses novel compounds of Formula (I): having 11β-HSD type 1 antagonist activity, as well as methods for preparing such compounds. In another embodiment, the invention discloses pharmaceutical compositions comprising compounds of Formula I, as well as methods of using the compounds and compositions to treat diabetes, hyperglycemia, obesity, hypertension, hyperlipidemia, metabolic syndrome, and other conditions associated with 11β-HSD type 1 activity.

(I)

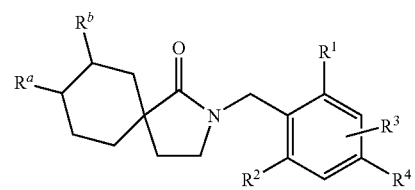

18 Claims, No Drawings

FOREIGN PATENT DOCUMENTS

| | | |
|---|---|---|
| WO | WO 2007/127765 | 11/2007 |
| WO | WO 2007/127901 | 11/2007 |
| WO | WO 2008/157752 | 12/2008 |

OTHER PUBLICATIONS

Yeh et al.: Discovery of orally active butyrolactam 11 β-HSD1 inhibitors, Bioorganic & Medicinal Chemistry Letters, Nov. 1, 2006, 16(21), pp. 5555-5560.

Schuster, Daniela et al.: The Discovery of New 11β-Hydroxysteroid Dehydrogenase Type 1 Inhibitors by Common Feature Pharmacophore Modeling and Virtual Screening, J. Medicinal Chemistry, 2006, 49, pp. 3454-3466.

Konno et al.: Electrolytic Partial Fluorination of Organic Compounds. 6. Highly Regioselective Electrochemical Monofluorination of Aliphatic Nitrogen-Containing Heterocycles, Tetrahedron Letters, 1992, vol. 33, No. 46, pp. 7017-7020.

* cited by examiner

INHIBITORS OF 11-BETA-HYDROXYSTEROID DEHYDROGENASE 1

This is the national phase application, under 35 USC 371, for PCT/US2007/067350, filed Apr. 25, 2007, which claims the benefit, under 35 USC 1.19(e), of US provisional application 60/745,574 filed Apr. 25, 2006.

This invention relates to compounds that are inhibitors of 11-β-hydroxysteroid dehydrogenase type 1 ("11-β-HSD1"), and to pharmaceutical compositions thereof, and the uses of these compounds and compositions in the treatment of the human or animal body, and to novel intermediates useful in preparation of the inhibitors. The present compounds show potent and selective inhibition of 11-β-HSD1, and as such are useful in the treatment of disorders responsive to the modulation of 11-β-HSD1, such as diabetes, metabolic syndrome, cognitive disorders, and the like.

Glucocorticoids acting in the liver, adipose tissue, and muscle, are important regulators of glucose, lipid, and protein metabolism. Chronic glucocorticoid excess is associated with insulin resistance, visceral obesity, hypertension, and dyslipidemia, which also represent the classical hallmarks of metabolic syndrome. 11-β-HSD1 catalyses the conversion of inactive cortisone to active cortisol, and has been implicated in the development of metabolic syndrome. Evidence in rodents and humans links 11-β-HSD1 to metabolic syndrome. Evidence suggests that a drug which specifically inhibits 11-β-HSD1 in type 2 diabetic patients will lower blood glucose by reducing hepatic gluconeogenesis, reduce central obesity, improve atherogenic lipoprotein phenotypes, lower blood pressure, and reduce insulin resistance. Insulin effects in muscle will be enhanced, and insulin secretion from the beta cells of the islet may also be increased. Evidence from animal and human studies also indicates that an excess of glucocorticoids impair cognitive function. Recent results indicate that inactivation of 11-β-HSD1 enhances memory function in both men and mice. The 11-β-HSD1 inhibitor carbenoxolone was shown to improve cognitive function in healthy elderly men and type 2 diabetics, and inactivation of the 11-β-HSD1 gene prevented aging-induced impairment in mice. Selective inhibition of 11-β-HSD1 with a pharmaceutical agent has recently been shown to improve memory retention in mice.

A number of publications have appeared in recent years reporting agents that inhibit 11-β-HSD1. See International Application WO2004/056744 which discloses adamantyl acetamides as inhibitors of 11-β-HSD, International Application WO2005/108360 which discloses pyrrolidin-2-one and piperidin-2-one derivatives as inhibitors of 11-β-HSD, and International Application WO2005/108361 which discloses adamantyl pyrrolidin-2-one derivatives as inhibitors of 11-β-HSD. In spite of the number of treatments for diseases that involve 11-β-HSD1, the current therapies suffer from one or more inadequacies, including poor or incomplete efficacy, unacceptable side effects, and contraindications for certain patient populations. Thus, there remains a need for an improved treatment using alternative or improved pharmaceutical agents that inhibit 11-β-HSD1 and treat the diseases that could benefit from 11-β-HSD1 inhibition. The present invention provides such a contribution to the art based on the finding that a novel class of compounds has a potent and selective inhibitory activity on 11-β-HSD1. The present invention is distinct in the particular structures and their activities. There is a continuing need for new methods of treating diabetes, metabolic syndrome, and cognitive disorders, and it is an object of this invention to meet these and other needs.

The present invention provides a compound structurally represented by formula I: The present invention provides a compound structurally represented by formula I:

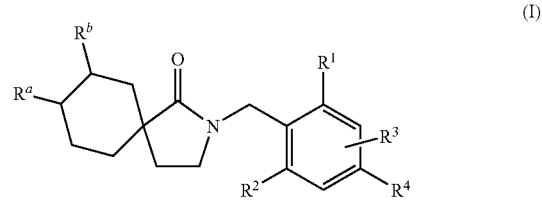

(I)

or a pharmaceutically acceptable salt thereof, wherein $R^a$ is —H or —OH;

$R^b$ is —H; or $R^a$ and $R^b$ combine with the cyclohexyl ring to which they are attached to form

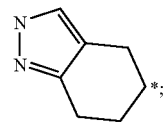

wherein the asterisk represents the carbon atom shared with the lactam ring of formula I;

$R^1$ is —H, -halogen, —O—CH$_3$ (optionally substituted with one to three halogens), or —CH$_3$ (optionally substituted with one to three halogens);

$R^2$ is —H, -halogen, —O—CH$_3$ (optionally substituted with one to three halogens), or —CH$_3$ (optionally substituted with one to three halogens);

$R^3$ is —H or -halogen;

$R^4$ is

—OH, -halogen, —CN, —(C$_1$-C$_4$)alkyl(optionally substituted with one to three halogens), —(C$_1$-C$_6$)alkoxy(optionally substituted with one to three halogens), —SCF$_3$, —C(O)O(C$_1$-C$_4$)alkyl, —O—CH$_2$—C(O)NH$_2$, —(C$_3$-C$_8$)cycloalkyl, —O-phenyl-C(O)O—(C$_1$-C$_4$)alkyl, —CH$_2$-phenyl, —NHSO$_2$—(C$_1$-C$_4$)alkyl, —NHSO$_2$-phenyl(R$^{21}$)(R$^{21}$), —(C$_1$-C$_4$)alkyl-C(O)N(R$^{10}$)(R$^{11}$),

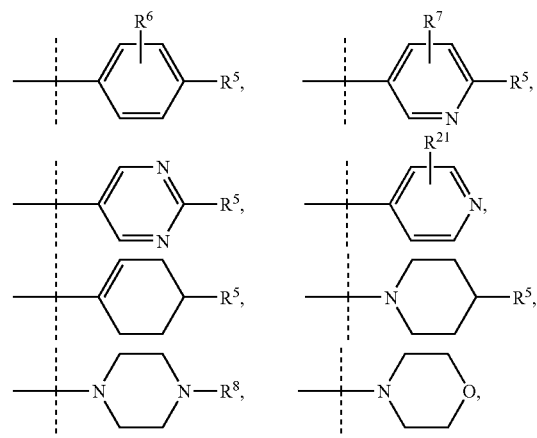

-continued

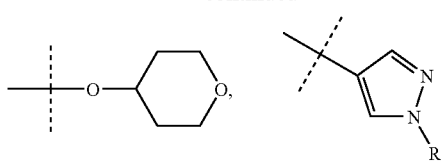
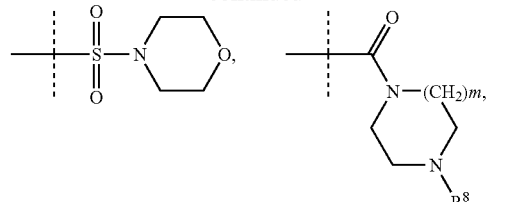
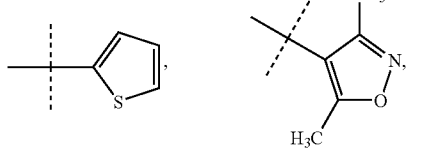

wherein the dashed line represents the point of attachment to the $R^4$ position in formula I;

$R^1$ is
—H, -halogen, —OH, —CN, —($C_1$-$C_4$)alkyl(optionally substituted with 1 to 3 halogens), —C(O)OH, —C(O)O—($C_1$-$C_4$)alkyl, —C(O)—($C_1$-$C_4$)alkyl,
—O—($C_1$-$C_4$)alkyl(optionally substituted with 1 to 3 halogens), —$SO_2$—($C_1$-$C_4$)alkyl, —N($R^8$)($R^8$), -phenyl($R^{21}$)($R^{21}$), —C(O)—NH—($C_3$-$C_6$)cycloalkyl,

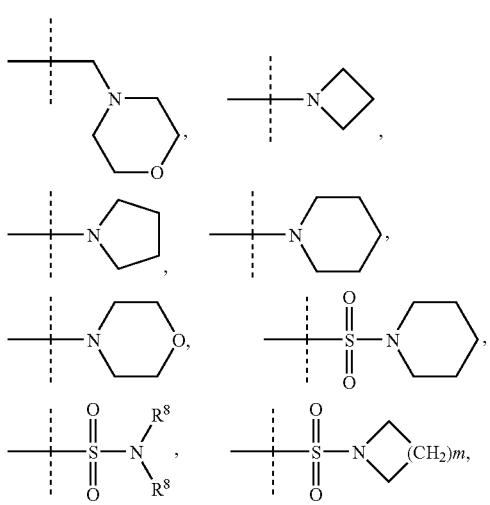

-continued

wherein the dashed line represents the point of attachment to the position indicated by $R^5$;
wherein m is 1, 2, or 3;
wherein n is 0, 1, or 2, and wherein when n is 0, then "($CH_2$)n" is a bond;

$R^6$ is
—H, -halogen, —CN, or —($C_1$-$C_4$)alkyl(optionally substituted with 1 to 3 halogens);

$R^7$ is
—H, -halogen, or —($C_1$-$C_4$)alkyl(optionally substituted with 1 to 3 halogens);

$R^8$ is independently at each occurrence —H or —($C_1$-$C_6$)alkyl(optionally substituted with 1 to 3 halogens);

$R^9$ is —H or -halogen;

$R^{10}$ and $R^{11}$ are each independently
—H or —($C_1$-$C_4$)alkyl, or $R^{10}$ and $R^{11}$ taken together with the nitrogen to which they are attached form piperidinyl, piperazinyl, or pyrrolidinyl;

$R^{20}$ is independently at each occurrence —H, or —($C_1$-$C_3$)alkyl(optionally substituted with 1 to 3 halogens);

$R^{21}$ is independently at each occurrence —H, -halogen, or —($C_1$-$C_3$)alkyl(optionally substituted with 1 to 3 halogens);

$R^{22}$ is independently at each occurrence —H or —$(C_1-C_6)$alkyl(optionally substituted with 1 to 3 halogens); and $R^{23}$ is independently at each occurrence —H, —$(C_1-C_4)$alkyl (optionally substituted with 1 to 3 halogens), or —C(O)O—$(C_1-C_4)$alkyl.

The present invention provides compounds of formula I that are useful as potent and selective inhibition of 11-β-HSD1. The present invention further provides a pharmaceutical composition which comprises a compound of Formula I, or a pharmaceutical salt thereof, and a pharmaceutically acceptable carrier, diluent, or excipient. In addition, the present invention provides a method for the treatment of metabolic syndrome, and related disorders, which comprise administering to a patient in need thereof an effective amount of a compound of formula I or a pharmaceutically acceptable salt thereof.

In one embodiment, the present invention provides compounds of Formula I or a pharmaceutically acceptable salt thereof as described in detail above. While all of the compounds of the present invention are useful, certain of the compounds are particularly interesting and are preferred. The following listings set out several groups of preferred compounds.

In another embodiment the invention provides a compound structurally represented by formula I, or a pharmaceutically acceptable salt thereof, wherein $R^a$ is —H or —OH;
$R^b$ is —H; or
$R^a$ and $R^b$ combine with the cyclohexyl ring to which they are attached to form

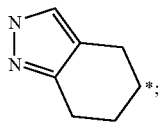

wherein the asterisk represents the carbon atom shared with the lactam ring of formula I;

$R^1$ is -halogen; $R^2$ is -halogen; $R^3$ is —H or -halogen;

$R^4$ is
—OH, -halogen, —CN, —$(C_1-C_4)$alkyl(optionally substituted with one to three halogens), —$(C_1-C_6)$alkoxy(optionally substituted with one to three halogens), —$SCF_3$, —$C(O)O(C_1-C_4)$alkyl, —O—$CH_2$—$C(O)NH_2$, —$(C_3-C_8)$cycloalkyl, —O-phenyl-C(O)O—$(C_1-C_4)$alkyl, —$CH_2$-phenyl, —$NHSO_2$—$(C_1-C_4)$alkyl, —$NHSO_2$-phenyl$(R^{21})(R^{21})$, —$(C_1-C_4)$alkyl-$C(O)N(R^{10})(R^{11})$,

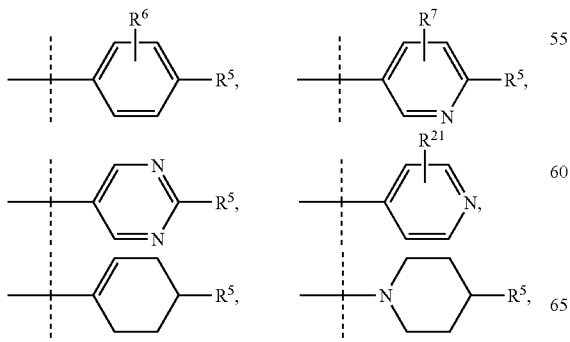

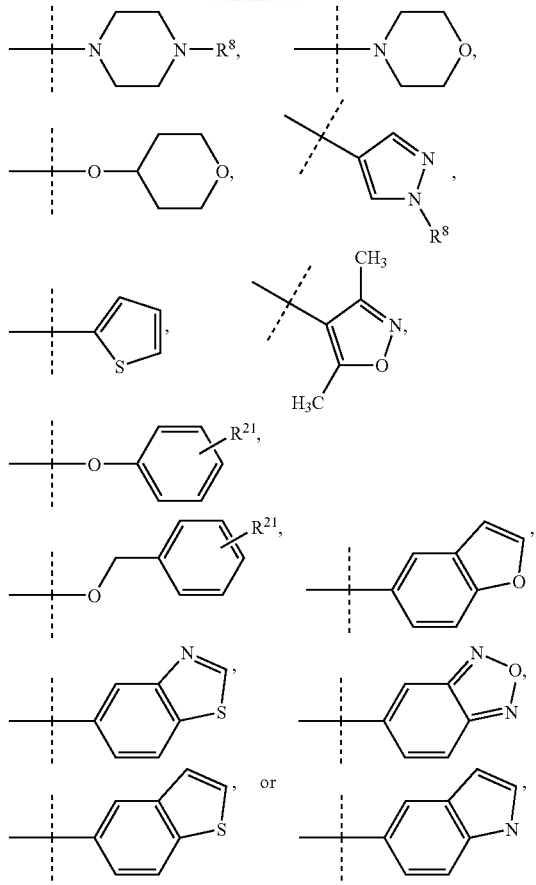

wherein the dashed line represents the point of attachment to the $R^4$ position in formula I;

$R^5$ is
—H, -halogen, —OH, —CN, —$(C_1-C_4)$alkyl(optionally substituted with 1 to 3 halogens), —C(O)OH, —C(O)O—$(C_1-C_4)$alkyl, —C(O)—$(C_1-C_4)$alkyl,
—O—$(C_1-C_4)$alkyl(optionally substituted with 1 to 3 halogens), —$SO_2$—$(C_1-C_4)$alkyl, —$N(R^8)(R^8)$, -phenyl$(R^{21})(R^{21})$, —C(O)—NH—$(C_3-C_6)$cycloalkyl,

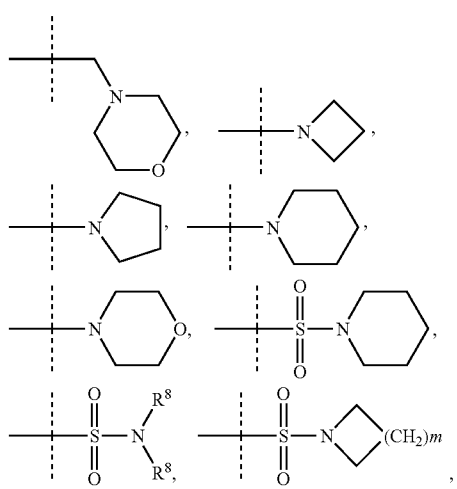

-continued

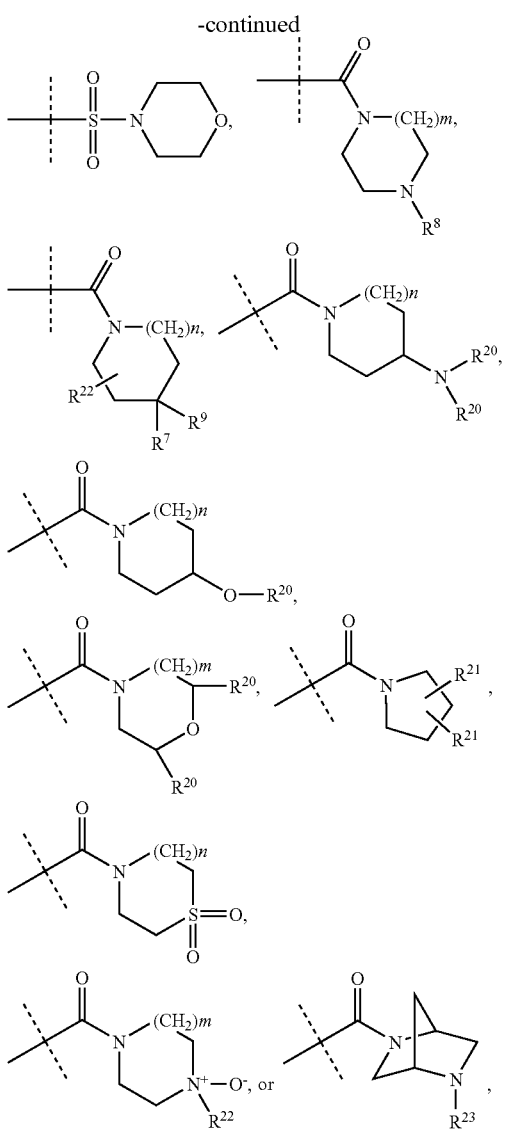

wherein the dashed line represents the point of attachment to the position indicated by $R^5$;
wherein m is 1, 2, or 3;
wherein n is 0, 1, or 2, and wherein when n is 0, then "$(CH_2)n$" is a bond;
$R^6$ is
—H, -halogen, —CN, or —$(C_1-C_4)$alkyl(optionally substituted with 1 to 3 halogens);
$R^7$ is
—H, -halogen, or —$(C_1-C_4)$alkyl(optionally substituted with 1 to 3 halogens);
$R^8$ is independently at each occurrence —H or —$(C_1-C_6)$alkyl(optionally substituted with 1 to 3 halogens);
$R^9$ is —H or -halogen;
$R^{10}$ and $R^{11}$ are each independently
—H or —$(C_1-C_4)$alkyl, or $R^{10}$ and $R^{11}$ taken together with the nitrogen to which they are attached form piperidinyl, piperazinyl, or pyrrolidinyl;
$R^{20}$ is independently at each occurrence —H, or —$(C_1-C_3)$alkyl(optionally substituted with 1 to 3 halogens);
$R^{21}$ is independently at each occurrence —H, -halogen, or —$(C_1-C_3)$alkyl(optionally substituted with 1 to 3 halogens);

$R^{22}$ is independently at each occurrence —H -$(C_1-C_6)$alkyl (optionally substituted with 1 to 3 halogens); and
$R^{23}$ is independently at each occurrence —H, —$(C_1-C_4)$alkyl (optionally substituted with 1 to 3 halogens), or —C(O)O—$(C_1-C_4)$alkyl.

In another embodiment the invention provides a compound structurally represented by formula I, or a pharmaceutically acceptable salt thereof, wherein
$R^a$ is —H or —OH;
$R^b$ is —H; or
$R^a$ and $R^b$ combine with the cyclohexyl ring to which they are attached to form

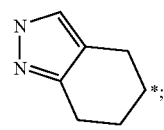

wherein the asterisk represents the carbon atom shared with the lactam ring of formula I;
$R^1$ is -chlorine, -fluorine, or -bromine; $R^2$ is -chlorine, -fluorine, or -bromine; $R^3$ is —H or -halogen;
$R^4$ is

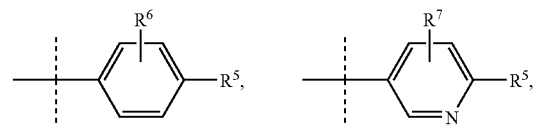

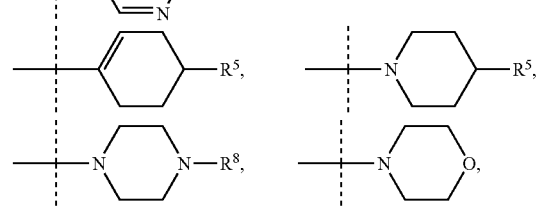

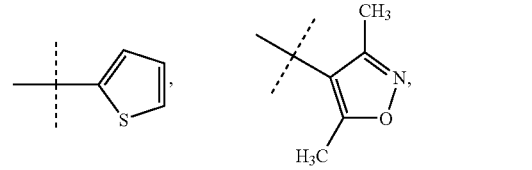

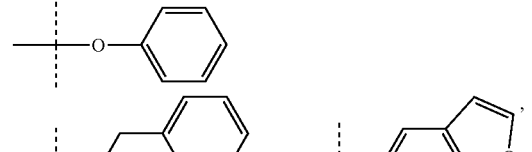

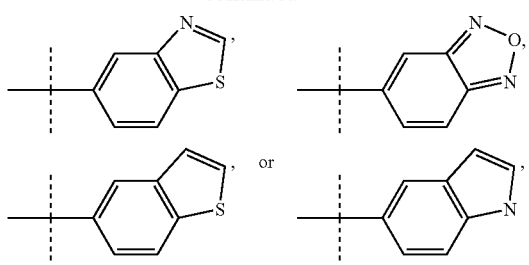

wherein the dashed line represents the point of attachment to the R⁴ position in formula I;

R⁵ is
—H, -halogen, —OH, —CN, —(C₁-C₄)alkyl(optionally substituted with 1 to 3 halogens), —C(O)OH, —C(O)O—(C₁-C₄)alkyl, —C(O)—(C₁-C₄)alkyl, —O—(C₁-C₄)alkyl(optionally substituted with 1 to 3 halogens), —SO₂—(C₁-C₄)alkyl, —N(R⁸)(R⁸), -phenyl(R²¹)(R²¹), —C(O)—NH—(C₃-C₆)cycloalkyl,

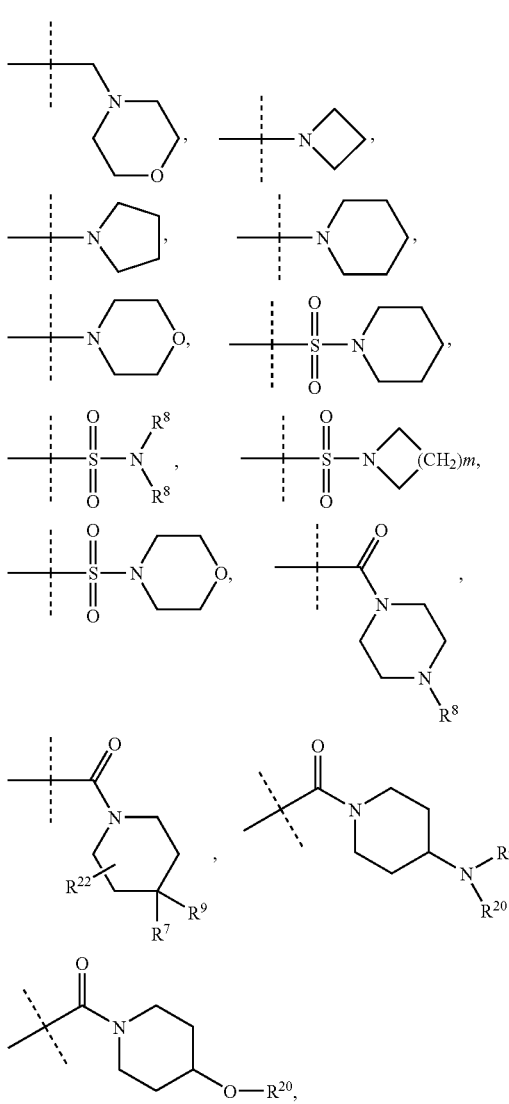

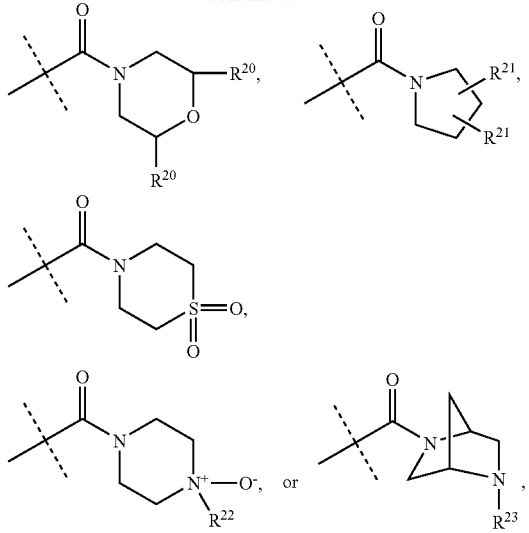

wherein the dashed line represents the point of attachment to the position indicated by R⁵; wherein m is 1, 2, or 3;

R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens);

R⁸ is independently at each occurrence —H or —(C₁-C₆)alkyl(optionally substituted with 1 to 3 halogens);

R⁹ is —H or -halogen;

R²⁰ is independently at each occurrence —H, or —(C₁-C₃)alkyl(optionally substituted with 1 to 3 halogens);

R²¹ is independently at each occurrence —H, -halogen, or —(C₁-C₃)alkyl(optionally substituted with 1 to 3 halogens);

R²² is independently at each occurrence —H or —(C₁-C₆)alkyl(optionally substituted with 1 to 3 halogens); and R²³ is independently at each occurrence —H, —(C₁-C₄)alkyl (optionally substituted with 1 to 3 halogens), or —C(O)O—(C₁-C₄)alkyl.

In another embodiment the invention provides a compound structurally represented by formula I, or a pharmaceutically acceptable salt thereof, wherein Rᵃ is —H or —OH;

Rᵇ is —H; or

Rᵃ and Rᵇ combine with the cyclohexyl ring to which they are attached to form

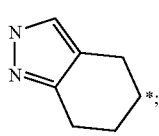

wherein the asterisk represents the carbon atom shared with the lactam ring of formula I;

R¹ is -chlorine, -fluorine, or -bromine; R² is -chlorine, -fluorine, or -bromine; R³ is —H or -halogen;

$R^4$ is

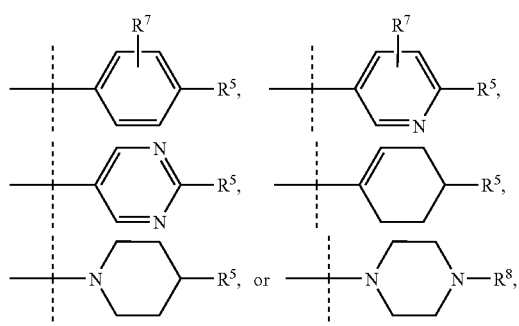

wherein the dashed line represents the point of attachment to the $R^4$ position in formula I;

$R^5$ is
—H, -halogen, —$(C_1$-$C_4)$alkyl(optionally substituted with 1 to 3 halogens), —C(O)OH, —C(O)O—$(C_1$-$C_4)$alkyl, —C(O)—$(C_1$-$C_4)$alkyl, —O—$(C_1$-$C_4)$alkyl(optionally substituted with 1 to 3 halogens), —$SO_2$—$(C_1$-$C_4)$alkyl, —$N(R^8)(R^8)$,

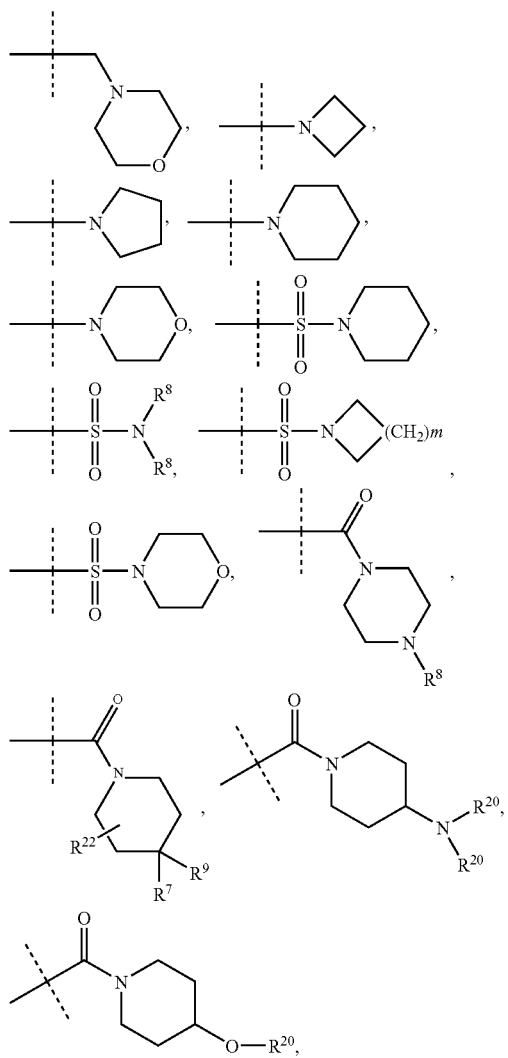

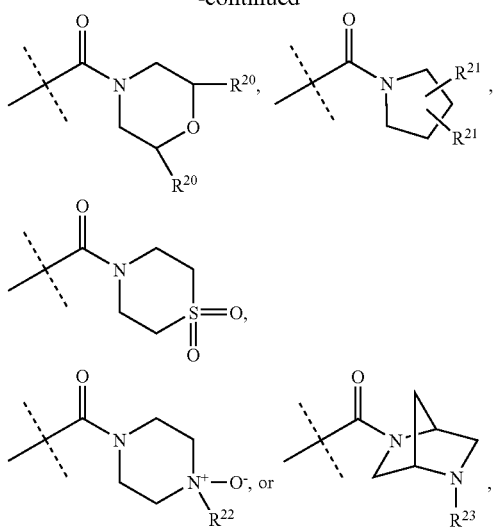

wherein the dashed line represents the point of attachment to the position indicated by $R^5$; wherein m is 1, 2, or 3;

$R^6$ is
—H, -halogen, —CN, or —$(C_1$-$C_4)$alkyl(optionally substituted with 1 to 3 halogens);

$R^7$ is
—H, -halogen, or —$(C_1$-$C_4)$alkyl(optionally substituted with 1 to 3 halogens);

$R^8$ is independently at each occurrence —H or —$(C_1$-$C_6)$alkyl(optionally substituted with 1 to 3 halogens);

$R^9$ is —H or -halogen;

$R^{20}$ is independently at each occurrence —H, or —$(C_1$-$C_3)$alkyl(optionally substituted with 1 to 3 halogens);

$R^{21}$ is independently at each occurrence —H, -halogen, or —$(C_1$-$C_3)$alkyl(optionally substituted with 1 to 3 halogens);

$R^{22}$ is independently at each occurrence —H or —$(C_1$-$C_6)$alkyl(optionally substituted with 1 to 3 halogens); and $R^{23}$ is independently at each occurrence —H, —$(C_1$-$C_4)$alkyl (optionally substituted with 1 to 3 halogens), or —C(O)O—$(C_1$-$C_4)$alkyl.

In another embodiment the invention provides a compound structurally represented by formula I, or a pharmaceutically acceptable salt thereof, wherein $R^a$ is —H or —OH;

$R^b$ is —H; or $R^a$ and $R^b$ combine with the cyclohexyl ring to which they are attached to form

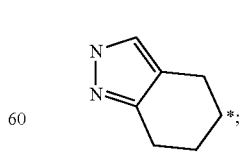

wherein the asterisk represents the carbon atom shared with the lactam ring of formula I;

$R^1$ is -chlorine, -fluorine, or -bromine; $R^2$ is -chlorine, -fluorine, or -bromine; $R^3$ is —H or -halogen;

$R^4$ is

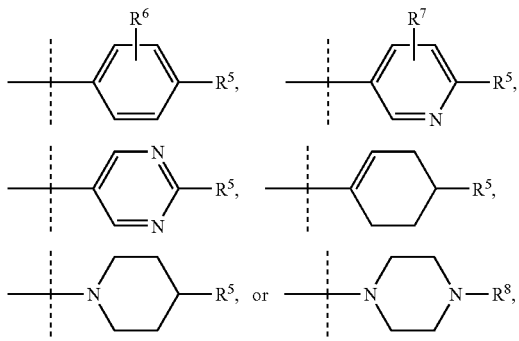

wherein the dashed line represents the point of attachment to the $R^4$ position in formula I;
$R^5$ is

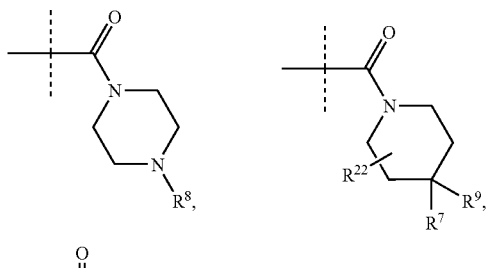

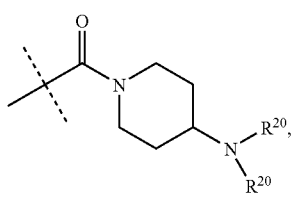

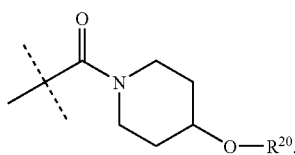

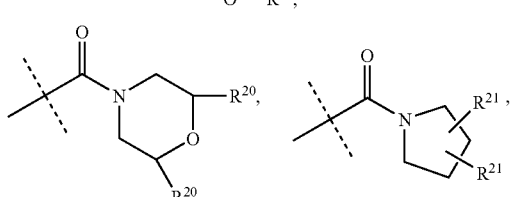

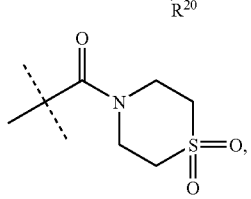

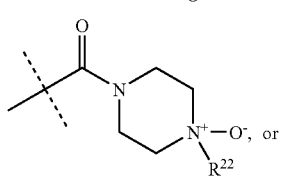, or

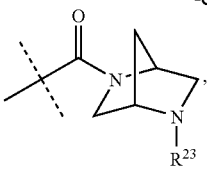

wherein the dashed line represents the point of attachment to the position indicated by $R^5$;
$R^6$ is
  —H, -halogen, —CN, or —($C_1$-$C_4$)alkyl(optionally substituted with 1 to 3 halogens);
$R^7$ is
  —H, -halogen, or —($C_1$-$C_4$)alkyl(optionally substituted with 1 to 3 halogens);
$R^8$ is independently at each occurrence —H or —($C_1$-$C_6$) alkyl(optionally substituted with 1 to 3 halogens);
$R^9$ is —H or -halogen;
$R^{20}$ is independently at each occurrence —H, or —($C_1$-$C_3$) alkyl(optionally substituted with 1 to 3 halogens);
$R^{21}$ is independently at each occurrence —H, -halogen, or —($C_1$-$C_3$)alkyl(optionally substituted with 1 to 3 halogens);
$R^{22}$ is independently at each occurrence —H or —($C_1$-$C_6$) alkyl(optionally substituted with 1 to 3 halogens); and
$R^{23}$ is independently at each occurrence —H, —($C_1$-$C_4$)alkyl (optionally substituted with 1 to 3 halogens), or —C(O)O—($C_1$-$C_4$)alkyl.

In another embodiment the invention provides a compound structurally represented by formula I, or a pharmaceutically acceptable salt thereof, wherein
$R^a$ is —H or —OH;
$R^b$ is —H; or
$R^a$ and $R^b$ combine with the cyclohexyl ring to which they are attached to form

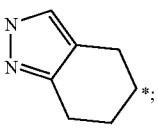

wherein the asterisk represents the carbon atom shared with the lactam ring of formula I;
$R^1$ is -chlorine, -fluorine, or -bromine; $R^2$ is -chlorine, -fluorine, or -bromine; $R^3$ is —H or -halogen;
$R^4$ is

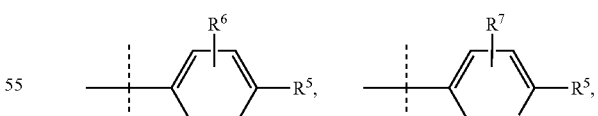

wherein the dashed line represents the point of attachment to the $R^4$ position in formula I;

R⁵ is
—SO₂—(C₁-C₄)alkyl,

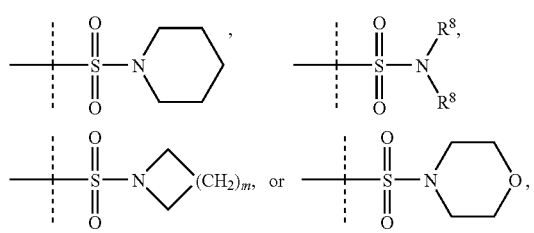

wherein the dashed line represents the point of attachment to the position indicated by R⁵; wherein m is 1, 2, or 3;

R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens); and R⁸ is independently at each occurrence —H or —(C₁-C₆)alkyl(optionally substituted with 1 to 3 halogens).

In another embodiment the invention provides a compound structurally represented by formula I, or a pharmaceutically acceptable salt thereof, wherein Rᵃ is —H or —OH;
Rᵇ is —H; or
Rᵃ and Rᵇ combine with the cyclohexyl ring to which they are attached to form

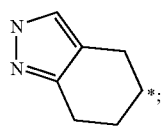

wherein the asterisk represents the carbon atom shared with the lactam ring of formula I;

R¹ is -chlorine, -fluorine, or -bromine; R² is -chlorine, -fluorine, or -bromine; R³ is —H or -halogen;

R⁴ is

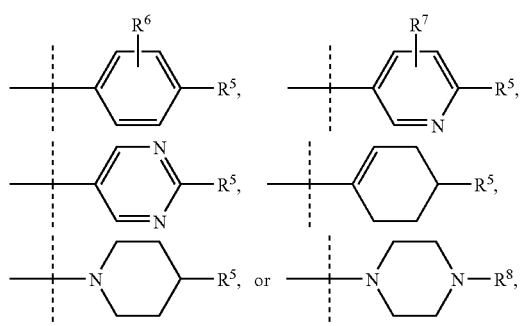

wherein the dashed line represents the point of attachment to the R⁴ position in formula I;

R⁵ is
—N(R⁸)(R⁸),

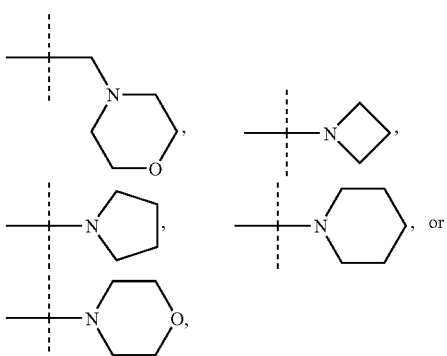

wherein the dashed line represents the point of attachment to the position indicated by R⁵;

R⁶ is
—H, -halogen, —CN, or —(C₁-C₄)alkyl(optionally substituted with 1 to 3 halogens);

R⁷ is
—H, -halogen, or —(C₁-C₄)alkyl(optionally substituted with 1 to 3 halogens); and R⁸ is independently at each occurrence —H or —(C₁-C₆)alkyl(optionally substituted with 1 to 3 halogens).

Other embodiments of the invention are provided wherein each of the embodiments described herein above is further narrowed as described in the following preferences. Specifically, each of the preferences below is independently combined with each of the embodiments above, and the particular combination provides another embodiment in which the variable indicated in the preference is narrowed according to the preference.

Preferably embodiments of the invention are structurally represented by the formula:

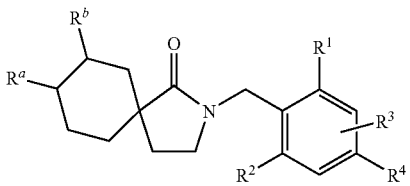

wherein Rᵃ is —OH. Preferably Rᵃ and Rᵇ combine with the cyclohexyl ring to which they are attached to form

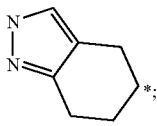

wherein the asterisk represents the carbon atom shared with the lactam ring of formula I.

Preferably R¹ is -halogen. Preferably R¹ is —CH₃. Preferably R¹ is -chlorine, -fluorine, or -bromine. Preferably R¹ is -chlorine. Preferably R¹ is -fluorine. Preferably R¹ is -bromine. Preferably R² is -halogen. Preferably R² is —CH₃. Preferably R² is -chlorine, -fluorine, or -bromine. Preferably R² is -chlorine. Preferably R² is -fluorine. Preferably R² is -bromine. Preferably R¹ is -chlorine and R² is -chlorine.

Preferably R³ is —H. Preferably R³ is -halogen. Preferably R¹ is -chlorine and R² is -chlorine, and R³ is —H.

Preferably R⁴ is

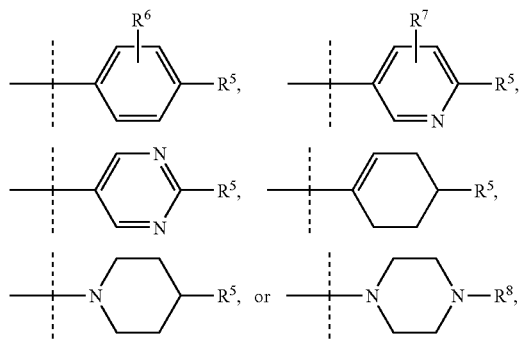

Preferably R⁴ is

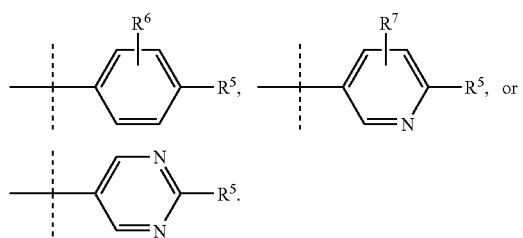

Preferably R⁴ is

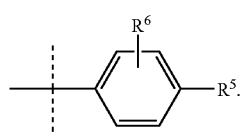

Preferably R⁴ is

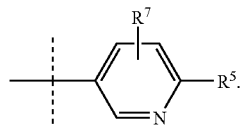

Preferably R⁴ is

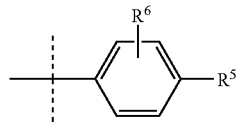

and R⁶ is —H. Preferably R⁴ is

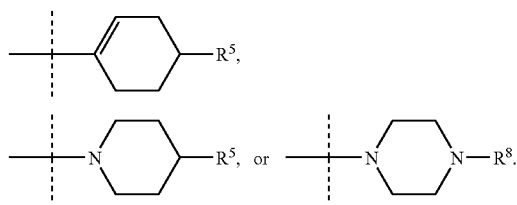

Preferably R⁴ is

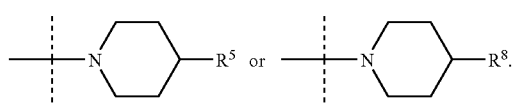

Preferably R⁴ is

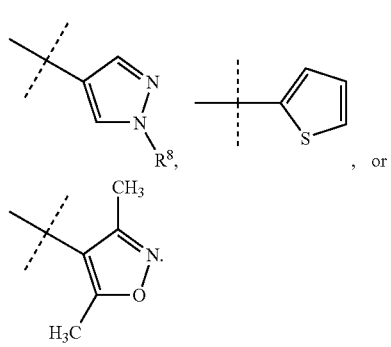

Preferably R⁴ is

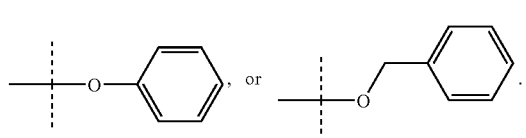

Preferably R⁴ is

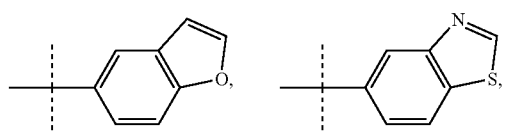

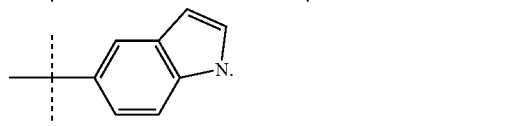

Preferably $R^5$ is —$N(R^8)(R^8)$
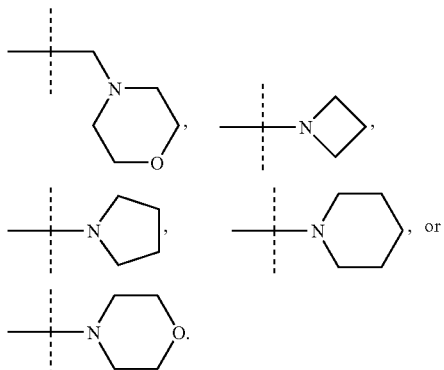
Preferably $R^5$ is —$SO_2$—$(C_1$-$C_4)$alkyl,
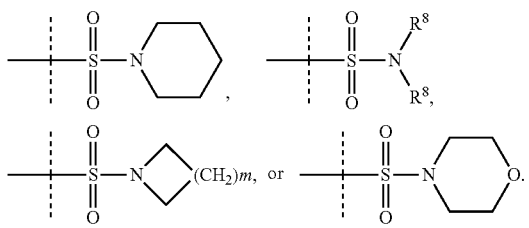
Preferably $R^5$ is
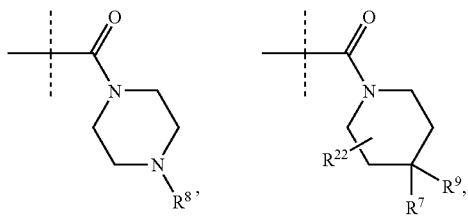
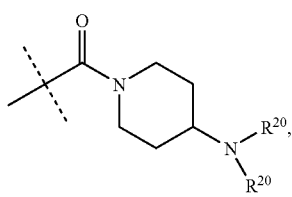
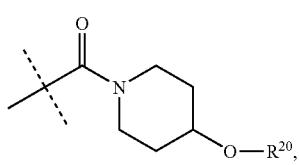
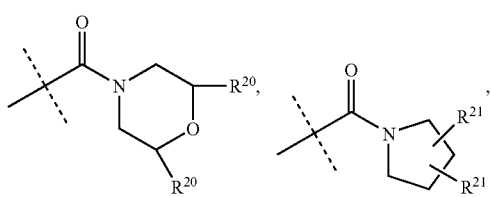
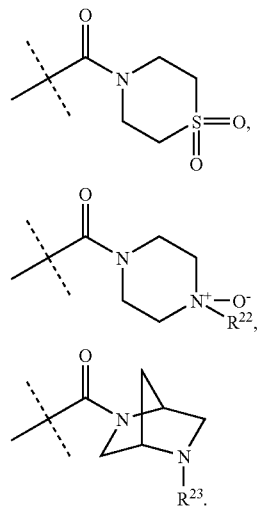
Preferably $R^5$ is
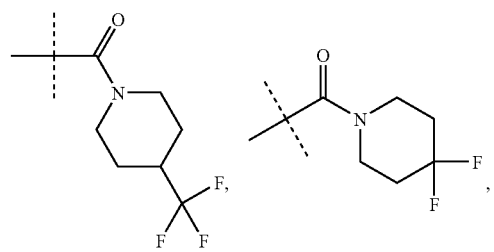
wherein $R^8$ is —$(C_1$-$C_3)$alkyl (optionally substituted with 1 to 3 halogens), or
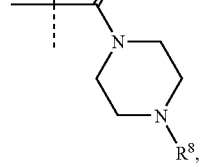
Preferably $R^5$ is
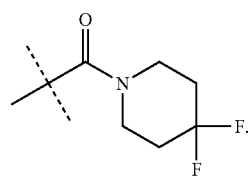

Preferably R⁵ is

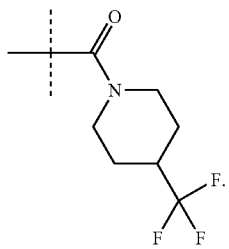

Preferably R⁵

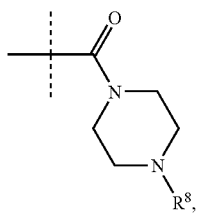

wherein R⁸ is —C₁-C₃)alkyl (optionally substituted with 1 to 3 halogens). Preferably R⁵ is chlorine or fluorine. Preferably R⁶ is —H. Preferably R⁶ is -halogen. Preferably R⁶ is —(C₁-C₄)alkyl(optionally substituted with 1 to 3 halogens). Preferably R⁷ is —H. Preferably R⁷ is -halogen, or —(C₁-C₄)alkyl (optionally substituted with 1 to 3 halogens). Preferably R⁷ is -halogen. Preferably R⁷ is —(C₁-C₄)alkyl(optionally substituted with 1 to 3 halogens).

Preferably R⁸ is independently at each occurrence —H. Preferably R⁸ is independently at each occurrence —(C₁-C₃) alkyl. Preferably R⁸ is independently at each occurrence —CH₃. Preferably R⁹ is —H. Preferably R⁹ is -halogen. Preferably R⁹ is —CF₃. Preferably R⁷ is -fluorine and R⁹ is -fluorine.

In another embodiment the invention provides a compound structurally represented by formula I, or a pharmaceutically acceptable salt thereof, wherein Rᵃ is —H or —OH; Rᵇ is —H; or Rᵃ and Rᵇ combine with the cyclohexyl ring to which they are attached to form

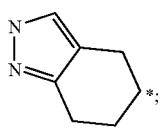

wherein the asterisk represents the carbon atom shared with the lactam ring of formula I;

R¹ is -chlorine; R² is -chlorine; R³ is —H;
R⁴ is
   -halogen,

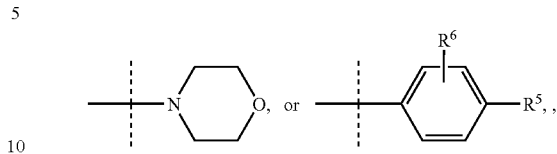

wherein the dashed line represents the point of attachment to the R⁴ position in formula I;
R⁵ is
   —H, -chlorine, -fluorine, —CH₃, —CF₃, —C(CH₃)₃, —CH(CH₃)₂, —O—C(CH₃)₂—C(O)O—CH₃, —N(—CH₃)(—CH₃),

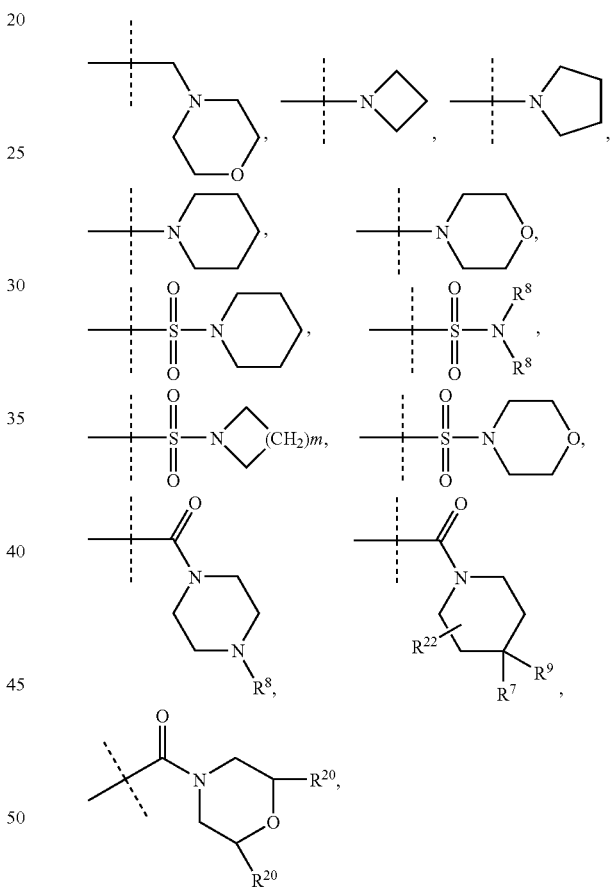

wherein the dashed line represents the point of attachment to the position indicated by R⁵; wherein m is 1, 2, or 3;
R⁶ is —H, -chlorine, -fluorine, -bromine, —CH₃, CF₃;
R⁷ is —H, -chlorine, -fluorine, -bromine;
R⁸ is independently at each occurrence —H or —CH₃, —CH₂—CH₃, —C(CH₃)₃, —CH(CH₃)₂;
R⁹ is —H or -chlorine, -fluorine, -bromine;
R²⁰ is independently at each occurrence —H, —CH₃; and
R²² is independently at each occurrence —H.

A preferred embodiment of the invention are compounds of the formula 2-[3,5-Dichloro-4'-(4-trifluoromethyl-piperidine-1-carbonyl)-biphenyl-4-ylmethyl]-2-aza-spiro[4.5]decan-1-one and 2-{3,5-Dichloro-4'-[4-(2-fluoro-ethyl)-piperazine-1-carbonyl]-biphenyl-4-ylmethyl}-2-aza-spiro[4.5]decan-1-one. A further embodiment of the invention are the novel intermediate preparations described herein which are useful for preparing the 11-β-HSD1 inhibitors according to formula I and the embodiments described herein. A further embodiment of the invention are the novel intermediate preparations described herein which are useful for preparing 2-[3,5-Dichloro-4'-(4-trifluoromethyl-piperidine-1-carbonyl)-biphenyl-4-ylmethyl]-2-aza-spiro[4.5]decan-1-one and 2-{3,5-Dichloro-4'-[4-(2-fluoro-ethyl)-piperazine-1-carbonyl]-biphenyl-4-ylmethyl}-2-aza-spiro[4.5]decan-1-one or a pharmaceutically acceptable salt thereof.

Patients with type 2 diabetes often develop "insulin resistance" which results in abnormal glucose homeostasis and hyperglycemia leading to increased morbidity and premature mortality. Abnormal glucose homeostasis is associated with obesity, hypertension, and alterations in lipid, lipoprotein, and apolipoprotein metabolism. Type 2 diabetics are at increased risk of developing cardiovascular complications, e.g., atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are important in the management and treatment of diabetes mellitus. Many patients who have insulin resistance but have not developed type 2 diabetes are also at risk of developing "Syndrome X" or "Metabolic syndrome". Metabolic syndrome is characterized by insulin resistance along with abdominal obesity, hyperinsulinemia, high blood pressure, low HDL, high VLDL, hypertension, atherosclerosis, coronary heart disease, and chronic renal failure. These patients are at increased risk of developing the cardiovascular complications listed above whether or not they develop overt diabetes mellitus.

Due to their inhibition of 11-β-HSD1, the present compounds are useful in the treatment of a wide range of conditions and disorders in which inhibition of 11-β-HSD1 is beneficial. These disorders and conditions are defined herein as "diabetic disorders" and "metabolic syndrome disorders". One of skill in the art is able to identify "diabetic disorders" and "metabolic syndrome disorders" by the involvement of 11-β-HSD1 activity either in the pathophysiology of the disorder, or in the homeostatic response to the disorder. Thus, the compounds may find use for example to prevent, treat, or alleviate, diseases or conditions or associated symptoms or sequalae, of "Diabetic disorders" and "metabolic syndrome disorders".

"Diabetic disorders" and "metabolic syndrome disorders" include, but are not limited to, diabetes, type 1 diabetes, type 2 diabetes, hyperglycemia, hyper insulinemia, beta-cell rest, improved beta-cell function by restoring first phase response, prandial hyperglycemia, preventing apoptosis, impaired fasting glucose (IFG), metabolic syndrome, hypoglycemia, hyper-hypokalemia, normalizing glucagon levels, improved LDL/HDL ratio, reducing snacking, eating disorders, weight loss, polycystic ovarian syndrome (PCOS), obesity as a consequence of diabetes, latent autoimmune diabetes in adults (LADA), insulitis, islet transplantation, pediatric diabetes, gestational diabetes, diabetic late complications, micro-macroalbuminuria, nephropathy, retinopathy, neuropathy, diabetic foot ulcers, reduced intestinal motility due to glucagon administration, short bowel syndrome, antidiarrheic, increasing gastric secretion, decreased blood flow, erectile dysfunction, glaucoma, post surgical stress, ameliorating organ tissue injury caused by reperfusion of blood flow after ischemia, ischemic heart damage, heart insufficiency, congestive heart failure, stroke, myocardial infarction, arrhythmia, premature death, anti-apoptosis, wound healing, impaired glucose tolerance (IGT), insulin resistance syndromes, metabolic syndrome, syndrome X, hyperlipidemia, dyslipidemia, hypertriglyceridemia, hyperlipoproteinemia, hypercholesterolemia, arteriosclerosis including atherosclerosis, glucagonomas, acute pancreatitis, cardiovascular diseases, hypertension, cardiac hypertrophy, gastrointestinal disorders, obesity, diabetes as a consequence of obesity, diabetic dyslipidemia, etc. Thus the present invention also provides a method of treatment of "Diabetic disorders" and "metabolic syndrome disorders" while reducing and or eliminating one or more of the unwanted side effects associated with the current treatments.

In addition, the present invention provides a compound of Formula I, or a pharmaceutical salt thereof, or a pharmaceutical composition which comprises a compound of Formula I, or a pharmaceutical salt thereof, and a pharmaceutically acceptable carrier, diluent, or excipient: for use in inhibiting 11-β-HSD1 activity; for use in inhibiting a 11-β-HSD1 activity mediated cellular response in a mammal; for use in reducing the glycemic level in a mammal; for use in treating a disease arising from excessive 11-β-HSD1 activity; for use in treating diabetic and other metabolic syndrome disorders in a mammal; and for use in treating diabetes, metabolic syndrome, obesity, hyperglycemia, atherosclerosis, ischemic heart disease, stroke, neuropathy, and wound healing. Thus, the methods of this invention encompass a prophylactic and therapeutic administration of a compound of Formula I.

The present invention further provides the use of a compound of Formula I, or a pharmaceutical salt thereof for the manufacture of a medicament for inhibiting 11-β-HSD1 activity; for the manufacture of a medicament for inhibiting 11-β-HSD1 activity mediated cellular response in a mammal; for the manufacture of a medicament for reducing the glycemic level in a mammal; for the manufacture of a medicament for treating a disease arising from excessive 11-β-HSD1 activity; for the manufacture of a medicament for treating diabetic and other metabolic syndrome disorders in a mammal; and for the manufacture of a medicament for preventing or treating diabetes, metabolic syndrome, obesity, hyperglycemia, atherosclerosis, ischemic heart disease, stroke, neuropathy, and improper wound healing.

The present invention further provides a method of treating conditions resulting from excessive 11-β-HSD1 activity in a mammal; a method of inhibiting 11-β-HSD1 activity in a mammal; a method of inhibiting a 11-β-HSD1 activity mediated cellular response in a mammal; a method of reducing the glycemic level in a mammal; a method of treating diabetic and other metabolic syndrome disorders in a mammal; a method of preventing or treating diabetes, metabolic syndrome, obesity, hyperglycemia, atherosclerosis, ischemic heart disease, stroke, neuropathy, and improper wound healing; said methods comprising administering to a mammal in need of such treatment a 11-β-HSD1 activity inhibiting amount of a compound of Formula I, or a pharmaceutically acceptable salt thereof, or a pharmaceutical composition which comprises a compound of Formula I, or a pharmaceutical salt thereof, and a pharmaceutically acceptable carrier, diluent, or excipient.

In addition, the present invention provides a pharmaceutical composition which comprises a compound of Formula I, or a pharmaceutical salt thereof, and a pharmaceutically acceptable carrier, diluent, or excipient: adapted for use in inhibiting 11-β-HSD1 activity; adapted for use in inhibiting 11-β-HSD1 activity mediated cellular responses; adapted for use in reducing the glycemic level in a mammal; adapted for use in treating diabetic and other metabolic syndrome disorders in a mammal; and adapted for use in preventing or treating diabetes, metabolic syndrome, obesity, hyperglycemia, atherosclerosis, ischemic heart disease, stroke, neuropathy, and wound healing.

In a further aspect of the invention the present compounds are administered in combination with one or more further active substances in any suitable ratios. Such further active substances may for example be selected from antidiabetics, antiobesity agents, antihypertensive agents, agents for the treatment of complications resulting from or associated with diabetes and agents for the treatment of complications and disorders resulting from or associated with obesity. The following listing sets out several groups of combinations. It will be understood that each of the agents named may be combined with other agents named to create additional combinations.

Thus, in a further embodiment of the invention the present compounds may be administered in combination with one or more antidiabetics.

Suitable antidiabetic agents include insulin, insulin analogues and derivatives such as those disclosed in EP 792 290 (Novo Nordisk A/S), for example $N^{\epsilon B29}$-tetradecanoyl des (B30) human insulin, EP 214 826 and EP 705 275 (Novo Nordisk A/S), for example Asp$^{B28}$ human insulin, U.S. Pat. No. 5,504,188 (Eli Lilly), for example Lys$^{B28}$ Pro$^{B29}$ human insulin, EP 368 187 (Aventis), for example Lantus®, GLP-1 and GLP-1 derivatives such as those disclosed in WO 98/08871 (Novo Nordisk A/S), as well as orally active hypoglycemic agents.

The orally active hypoglycemic agents preferably comprise imidazolines, sulphonylureas, biguanides, meglitinides, oxadiazolidinediones, thiazolidinediones, insulin sensitizers, insulin secretagogues, such as glimepiride, α-glucosidase inhibitors, agents acting on the ATP-dependent potassium channel of the β-cells for example potassium channel openers such as those disclosed in WO 97/26265, WO 99/03861 and WO 00/37474 (Novo Nordisk A/S), or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), GLP-1 antagonists, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, activators of glucokinase (GK) such as those disclosed in WO 00/58293, WO 01/44216, WO 01/83465, WO 01/83478, WO 01/85706, WO 01/85707, and WO 02/08209 (Hoffman-La Roche) or those disclosed in WO 03/00262, WO 03/00267 and WO 03/15774 (AstraZeneca), GSK-3 (glycogen synthase kinase-3) inhibitors, compounds modifying the lipid metabolism such as antilipidemic agents such as HMG CoA inhibitors (statins), compounds lowering food intake, PPAR (Peroxisome proliferator-activated receptor) ligands including the PPAR-alpha, PPAR-gamma and PPAR-delta subtypes, and RXR (retinoid X receptor) agonists, such as ALRT-268, LG-1268 or LG-1069.

In another embodiment, the present compounds are administered in combination with insulin or an insulin analogue or derivative, such as $N^{\epsilon B29}$-tetradecanoyl des (B30) human insulin, Asp$^{B28}$ human insulin, Lys$^{B28}$ Pro$^{B29}$ human insulin, Lantus®, or a mix-preparation comprising one or more of these.

In a further embodiment of the invention the present compounds are administered in combination with a sulphonylurea such as glibenclamide, glipizide, tolbautamide, chloropamidem, tolazamide, glimepride, gliclazide and glyburide.

In another embodiment of the invention the present compounds are administered in combination with a biguanide, for example, metformin.

In yet another embodiment of the invention the present compounds are administered in combination with a meglitinide, for example, repaglinide or nateglinide.

In still another embodiment of the invention the present compounds are administered in combination with a thiazolidinedione insulin sensitizer, for example, troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation).

In still another embodiment of the invention the present compounds may be administered in combination with an insulin sensitizer, for example, such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 such as ragaglitazar (NN 622 or (−)DRF 2725) (Dr. Reddy's Research Foundation) and WO 00/23425, WO 00/23415, WO 00/23451, WO 00/23445, WO 00/23417, WO 00/23416, WO 00/63153, WO 63196, WO 00/63209, WO 00/63190 and WO 00/63189 (Novo Nordisk A/S).

In a further embodiment of the invention the present compounds are administered in combination with an α-glucosidase inhibitor, for example, voglibose, emiglitate, miglitol or acarbose.

In another embodiment of the invention the present compounds are administered in combination with an agent acting on the ATP-dependent potassium channel of the β-cells, for example, tolbutamide, glibenclamide, glipizide, gliclazide, BTS-67582 or repaglinide.

In yet another embodiment of the invention the present compounds may be administered in combination with nateglinide.

In still another embodiment of the invention the present compounds are administered in combination with an antilipidemic agent or antihyperlipidemic agent for example cholestyramine, colestipol, clofibrate, gemfibrozil, lovastatin, pravastatin, simvastatin, pitavastatin, rosuvastatin, probucol, dextrothyroxine, fenofibrate or atorvastin.

In still another embodiment of the invention the present compounds are administered in combination with compounds lowering food intake.

In another embodiment of the invention, the present compounds are administered in combination with more than one of the above-mentioned compounds for example in combination with metformin and a sulphonylurea such as glyburide; a sulphonylurea and acarbose; nateglinide and metformin; repaglinide and metformin, acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

General terms used in the description of compounds herein described bear their usual meanings.

As used herein, the terms "$(C_1-C_3)$alkyl", "$(C_1-C_4)$alkyl" or "$(C_1-C_6)$alkyl" refer to straight-chain or branched-chain saturated aliphatic groups of the indicated number of carbon atoms, such as methyl, ethyl, n-propyl, isopropyl, n-butyl, isobutyl, sec-butyl, t-butyl, and the like. The term "$(C_1-C_6)$ alkoxy" represents a $C_1-C_6$ alkyl group attached through an oxygen and include moieties such as, for example, methoxy, ethoxy, n-propoxy, isopropoxy, and the like. The term "halogen" refers to fluoro, chloro, bromo, and iodo. The term "($C_3$-$C_8$) cycloalkyl" refers to a saturated or partially saturated carbocycle ring of from 3 to 8 carbon atoms, typically 3 to 7 carbon atoms. Examples of ($C_3$-$C_8$) cycloalkyl include but are not limited to cyclopropyl, cyclobutyl, cyclopentyl, cyclohexyl, cycloheptyl, and the like.

The term "optionally substituted," or "optional substitutents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structural formulae, and upon such occurrence each term shall be defined independently of the other.

It is understood that guinea pigs, dogs, cats, rats, mice, hamsters, and primates, including humans, are examples of patients within the scope of the meaning of the term "patient". Preferred patients include humans. The term "patient" includes livestock animals. Livestock animals are animals raised for food production. Ruminants or "cud-chewing" animals such as cows, bulls, heifers, steers, sheep, buffalo, bison, goats and antelopes are examples of livestock. Other examples of livestock include pigs and avians (poultry) such as chickens, ducks, turkeys and geese. The patient to be treated is preferably a mammal, in particular a human being.

The terms "treatment", "treating" and "treat", as used herein, include their generally accepted meanings, i.e., the management and care of a patient for the purpose of preventing, reducing the risk in incurring or developing a given condition or disease, prohibiting, restraining, alleviating, ameliorating, slowing, stopping, delaying, or reversing the progression or severity, and holding in check and/or treating existing characteristics, of a disease, disorder, or pathological condition, described herein, including the alleviation or relief of symptoms or complications, or the cure or elimination of the disease, disorder, or condition. The present method includes both medical therapeutic and/or prophylactic treatment, as appropriate.

As used herein, the term "therapeutically effective amount" means an amount of compound of the present invention that is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated.

"Composition" means a pharmaceutical composition and is intended to encompass a pharmaceutical product comprising the active ingredient(s) including compound(s) of Formula I, and the inert ingredient(s) that make up the carrier. Accordingly, the pharmaceutical compositions of the present invention encompass any composition made by admixing a compound of the present invention and a pharmaceutically acceptable carrier.

The term "suitable solvent" refers to any solvent, or mixture of solvents, inert to the ongoing reaction that sufficiently solubilizes the reactants to afford a medium within which to effect the desired reaction.

The term "unit dosage form" means physically discrete units suitable as unitary dosages for human subjects and other non-human animals, each unit containing a predetermined quantity of active material calculated to produce the desired therapeutic effect, in association with a suitable pharmaceutical carrier.

The compounds of the present invention may have one or more chiral centers and may exist in a variety of stereoisomeric configurations. As a consequence of these chiral centers the compounds of the present invention can occur as racemates, as individual enantiomers or mixtures of enantiomers, as well as diastereomers and mixtures of diastereomers. All such racemates, enantiomers, diastereomers and mixtures are within the scope of the present invention, whether pure, partially purified, or unpurified mixtures. For the examples provided herein, when a molecule which contains a chiral center or centers of known configuration is presented, its stereochemistry is designated in the name and in the structural representation of the molecule. If the stereochemistry is unknown or undefined its stereochemistry is not designated in the name or in the structural representation of the molecule. Embodiments of the invention include the Examples provided herein, and although the Example provided may be of one chiral or conformational form, or a salt thereof, further embodiments of the invention include all other stereoisomeric and or conformational forms of the examples described, as well as pharmaceutically acceptable salts thereof. These embodiments include any isolated enantiomers, diastereomers, and or conformers of these structures, as well as any mixtures containing more than one form.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention. Furthermore, some of the compounds of the present invention may exist in different tautomeric forms and it is intended that any tautomeric forms which the compounds are able to form are included within the scope of the present invention.

The term "enantiomeric enrichment" as used herein refers to the increase in the amount of one enantiomer as compared to the other. A convenient method of expressing the enantiomeric enrichment achieved is the concept of enantiomeric excess, or ee which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

When a compound of formula (I) is designated by "cis" or "trans", the designation describes the relative position of the carbonyl to $R^a$ in the 2-aza-spiro[4.5]decan-1-one core.

A compound designated as "trans" has the following relative position of $R^{a1}$ to the carbonyl in compound II and III, wherein $R^{a1}$ is —OH, and —O-Pg, where Pg is a protecting group, for example —Si(phenyl)$_2$-C(CH$_3$)$_3$:

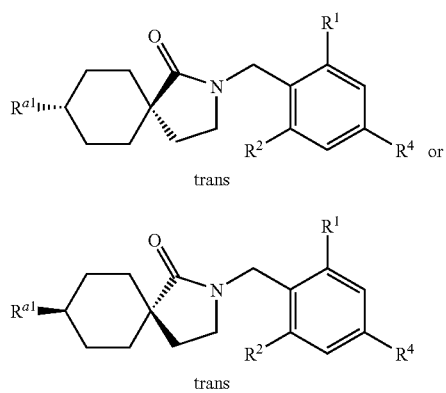

A compound designated as "cis" has the following relative position of $R^{a1}$ to the carbonyl in compound IV and V, wherein $R^{a1}$ is —OH, and —O-Pg, where Pg is a protecting group, for example —Si(phenyl)$_2$-C(CH$_3$)$_3$:

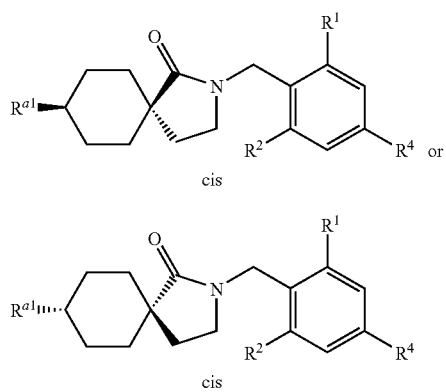

The compounds of Formula I, can be prepared by one of ordinary skill in the art following a variety of procedures, some of which are illustrated in the procedures and schemes set forth below. The particular order of steps required to produce the compounds of Formula I is dependent upon the particular compound to being synthesized, the starting compound, and the relative liability of the substituted moieties. The reagents or starting materials are readily available to one of skill in the art, and to the extent not commercially available, are readily synthesized by one of ordinary skill in the art following standard procedures commonly employed in the art, along with the various procedures and schemes set forth below.

The following Schemes, Preparations, Examples and Procedures are provided to better elucidate the practice of the present invention and should not be interpreted in any way as to limit the scope of the same. Those skilled in the art will recognize that various modifications may be made while not departing from the spirit and scope of the invention. All publications mentioned in the specification are indicative of the level of those skilled in the art to which this invention pertains.

The optimal time for performing the reactions of the Schemes, Preparations, Examples and Procedures can be determined by monitoring the progress of the reaction via conventional chromatographic techniques. Furthermore, it is preferred to conduct the reactions of the invention under an inert atmosphere, such as, for example, argon, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of Formula I may be further purified, if desired by common techniques such as recrystallization or chromatography over solid supports such as silica gel or alumina.

The skilled artisan will appreciate that not all substituents are compatible with all reaction conditions. These compounds may be protected or modified at a convenient point in the synthesis by methods well known in the art.

The terms and abbreviations used in the instant Schemes, Preparations, Examples and Procedures have their normal meanings unless otherwise designated. For example, as used herein, the following terms have the meanings indicated: "psi" refers to pounds per square inch; "TLC" refers to thin layer chromatography; "HPLC" refers to high performance liquid chromatography; "R$_f$" refers to retention factor; "R$_t$" refers to retention time; "δ" refers to part per million downfield from tetramethylsilane; "MS" refers to mass spectrometry, Observed Mass indicates [M+H] unless indicated otherwise. "MS(APCi) refers to atmospheric pressure chemical ionization mass spectrometry, "UV" refers to ultraviolet spectrometry, "$^1$H NMR" refers to proton nuclear magnetic resonance spectrometry. "LCMS" refers to liquid chromatography-mass spectrometry, "GC/MS" refers to gas chromatography/mass spectrometry. "IR" refers to infra red spectrometry, and the absorption maxima listed for the IR spectra are only those of interest and not all of the maxima observed. "RT" refers to room temperature.

"THF" refers to tetrahydrofuran, "LAH" refers to lithium aluminum hydride, "LDA" refers to lithium diisopropylamide, "DMSO" refers to dimethylsulfoxide, "DMF" refers to dimethylformamide, "EtOAc" refers to ethyl acetate, "Pd—C" refers to palladium on carbon, "DCM" refers to dichloromethane, "DMAP" refers to dimethylaminopyridine, "LiHMDS" refers to Lithium Hexamethyldisilisane, "TFA" refers to trifluoroacetic acid, "EDAC" refers to N-Ethyl-N'-(3-dimethylaminopropyl)carbodiimide hydrochloride, "HOBT" refers to 1-Hydroxy benzotriazole, "Bn-9-BBN" refers to Benzyl-9-borabicyclo[3.3.1]nonane, "Pd(dppf)Cl$_2$" refers to [1,1'-Bis(diphenylphosphino)-ferrocene) dichloropalladium(II),"EDCI" refers to N-Ethyl-N'-(3-dimethylaminopropyl)carbodiimide hydrochloride, "DBU" refers to 1,8-

Diazabicyclo[5.4.0]undecene-7, "TBSCl" refers to tert-butyl-dimethyl-silanyloxymethyl chloride, "NBS" refers to N-Bromosuccinimide, "TsOH" refers to p-toluenesulfonic acid, "DCE" refers to dichloroethane, "DAST" refers to (Diethylamino)sulfur trifluoride, "EA/H" refers to ethyl acetate/hexanes mixture, "Pd$_2$(dba)$_3$" refers to Bis(dibenzylideneacetone)palladium, "BINAP" refers to 2,2'-Bis(diphenylphosphino-1,1'-binaphthalene, "NMP" refers to N-Methylpyrrollidine, "TMSCN" refers to Trimethylsilyl cyanide, "TBAF" refers to Tetrabutylammonium fluoride, "Tf$_2$O" refers to trifluoromethanesulfonic anhydride, "TBSO" refers to tert-butyl-dimethyl-silanyloxy, "OTf" refers to trifluoromethanesulfonate, MeTi(Oi—Pr)$_3$ refers to methyltitanium triisopropoxide, "BBr$_3$" refers to boron tribromide, "PBr$_3$" refers to phosphorous tribromide, "Pd(PPh$_3$)$_4$" refers to tetrakis(triphenylphosphine)palladium (0), "OAc" refers to acetate, "DME" refers to dimethylethane, "Et$_2$O" refers to diethyl ether, "(Ph$_3$P)$_4$Pd" refers to tetrakis(triphenylphosphine)palladium (0), "DMFDMA" refers to N,N-dimethylformamide dimethyl acetal, "Et$_3$N" refers to triethylamine, "tBu" refers to t-butyl, "DIPEA" refers to diisopropylethyl amine, "EDC" refers to -(3-Dimethylaminopropyl)-3-ethylcarbodiimide hydrochloride, "HOAc" refers to acetic acid, "boc" refers to t-butoxycarbonyl. In a structure, "Ph" refers to phenyl, "Me" refers to methyl, "Et" refers to ethyl, "Bn" refers to benzyl, "MeOH" refers to methanol, "OTf" refers to trifluoromethanesulfonate, "TIPSO" refers to triisopropylsilanyloxy, "TBSO" refers to tert-butyl-dimethyl-silanyloxy.

The Examples provided herein are illustrative of the invention claimed herein and are not intended to limit the scope of the claimed invention in any way. The preparations and examples are named using AutoNom 2.2 in ChemDraw Ultra, or AutoNom 2000 in MDL ISIS/Draw version 2.5 SPI from MDL Information Systems, Inc., or are provided by Chemical Abstracts Services.

A Varian INOVA 400 MHz spectrometer is used to obtain $^1$H NMR Specta the in the solvent indicated. An Agilent HP1100 instrument equipped with a Mass Spectrometer (Agilent MSD SL) is used to obtain LCMS. A Waters Xterra C18 (2.1×50 mm, 3.5 micron) is used as stationary phase and a standard method is a gradient of 5-100% acetonitrile/methanol (50:50) with 0.2% ammonium formate over 3.5 minutes then held at 100% B for 0.5 minutes at a column temperature of 50° C. and a flow rate of 1.0 mL/min. Another standard method is a gradient of 5-100% acetonitrile/methanol (50:50) with 0.2% ammonium formate over 7.0 minutes then held at 100% B for 1.0 minutes at a column temperature of 50° C. and a flow rate of 1.0 mL/min. Additional MS analysis via Agilent MSD (loop machine) is standard Flow injection Analysis (FIA), no column is present and flow is 0.5 ml/min of 80% MeOH with 6.5 mM Ammonium Acetate for 30 secs run time.

Scheme A

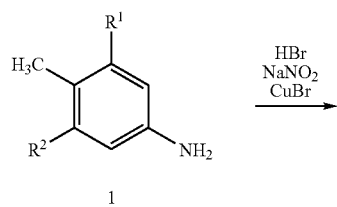

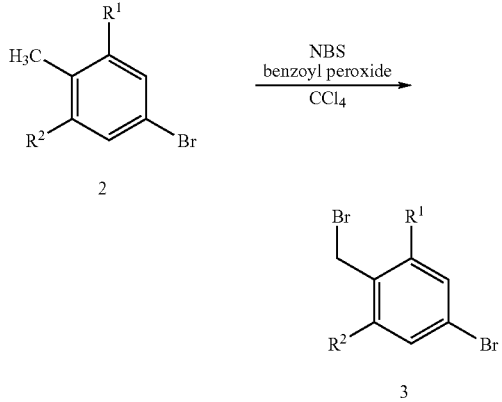

In Scheme A, an optionally substituted aniline is converted to compound 2 and then to compound 3 which has a leaving group (Lg). Preferably, compound 2 is treated with N-bromosuccinimide to form the bromomethyl compound.

Scheme B

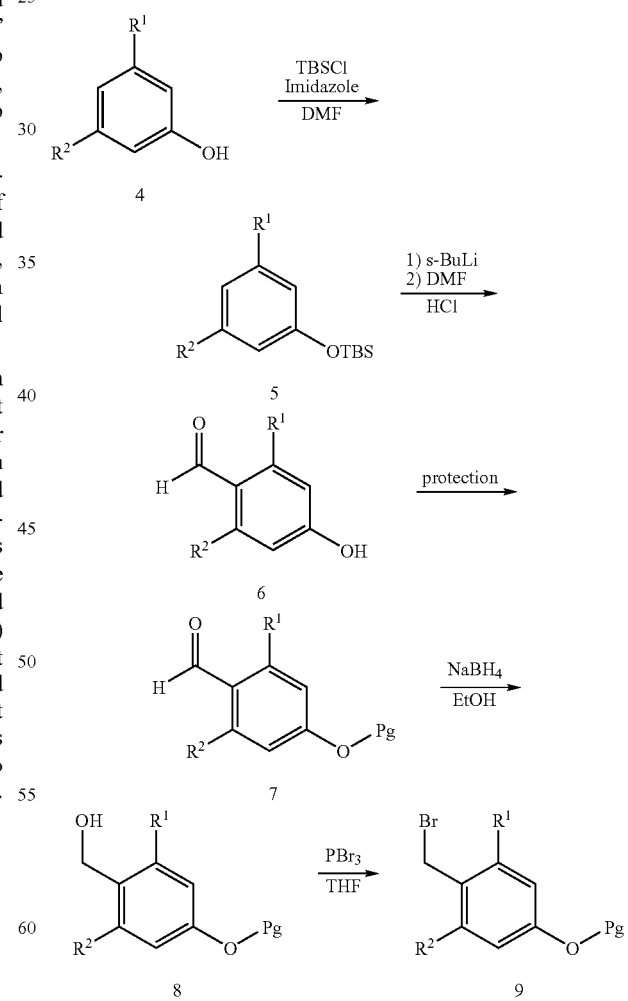

In Scheme B, an optionally substituted phenol (4) is protected (e.g., with TBSCl) to form compound 5, and then compound 5 is converted to the aldehyde (6). Compound 6 is reacted with a compound containing a protecting group (Pg) and leaving group (Lg) to give the ether compound 7. Pg can be —CH₃ or —CH₂-phenyl and Lg can be mesylate or halo. Preferably, the Lg-Pg compound is ICH₃ or Br—CH₂-phenyl. The aldehyde is reduced to form the alcohol (8) and then converted to compound 9. Preferably, compound 8 is halogenated with PBr₃ to give the 2-bromo-methyl compound.

Protection and deprotection of the compounds to form compounds of formula Ia and others are well known to the skilled artisan and are described in the literature. (For example, see: Greene and Wuts, *Protective Groups in Organic Synthesis*, Third Edition, John Wiley and Sons Inc., 1999).

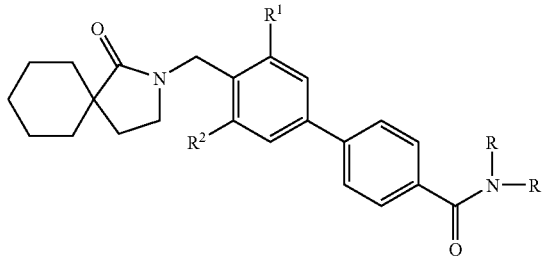

16

In Scheme C, a cyclohexane carboxylate ester (10) is reacted with a base such as LDA and is alkylated in a non-protic solvent (preferably THF) with bromoacetonitrile to form compound (11). Nitrile (11) is reduced and cyclized to afford (12) as described in the literature (see Reddy, P. A.; Hsiang, B. C. H.; Latifi, T. N.; Hill, M. W.; Woodward K. E.; Rothman, S. M.; Ferrendelli, J. A.; Covey, D. F. J. Med. Chem. 1996, 39, 1898-1906). Compound (12) is treated with a base (preferably NaH) and is alkylated with (3) to form (13). A coupling reaction is performed on (13) using a phenylboronic acid reagent and a catalyst, such as palladium tetrakistriphenylphosphine to prepare ester (14). Hydrolysis of (14) affords acid (15) which is coupled with an amine using standard amide coupling conditions such as 1,1'-carbonyldiimidazole to afford (16).

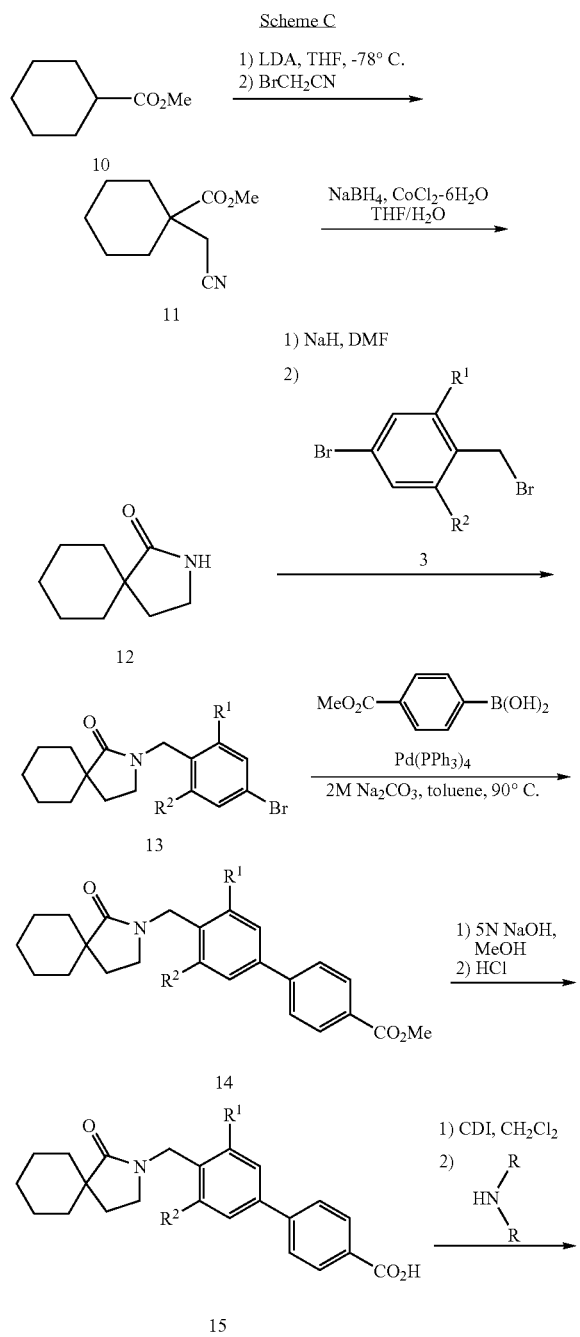

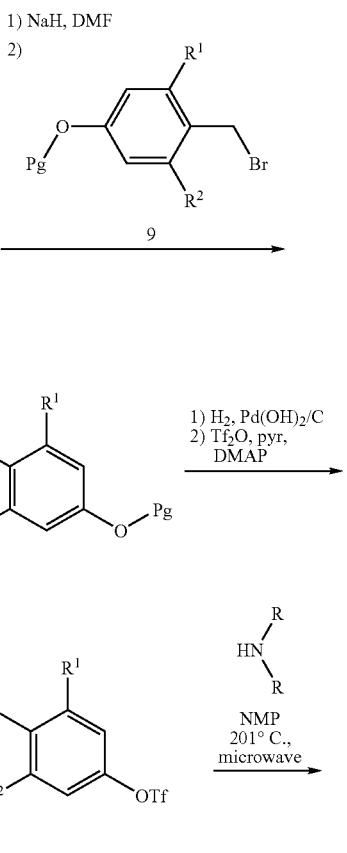

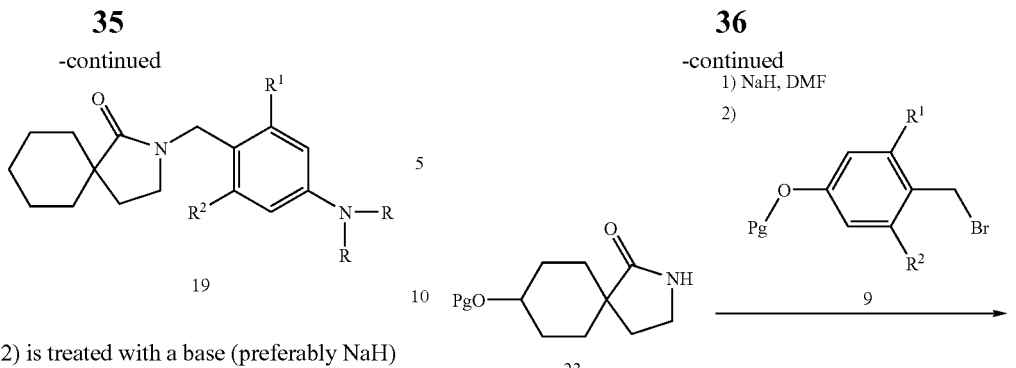

In Scheme D, (12) is treated with a base (preferably NaH) and is alkylated with (9) to form (17). Compound (17) is deprotected by a suitable method, such as using hydrogen with a catalyst, and the resulting phenol is reacted with triflic anhydride (trifluoromethanesulfonic anhydride) and a base, for example pyridine to prepare (18). Triflate 18 is reacted with an amine such as morpholine in NMP (1-methyl-2-pyrrolidinone) to afford (19) as described in the literature (see Xu G.; Wang, Y. G. *Org. Lett.* 2004, 6, 985-987).

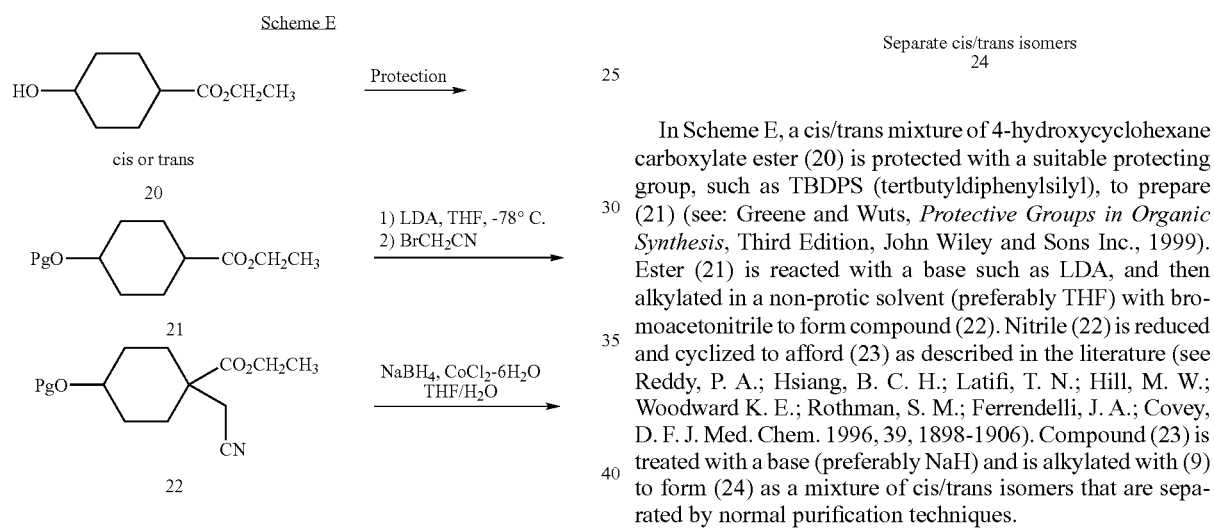

In Scheme E, a cis/trans mixture of 4-hydroxycyclohexane carboxylate ester (20) is protected with a suitable protecting group, such as TBDPS (tertbutyldiphenylsilyl), to prepare (21) (see: Greene and Wuts, *Protective Groups in Organic Synthesis*, Third Edition, John Wiley and Sons Inc., 1999). Ester (21) is reacted with a base such as LDA, and then alkylated in a non-protic solvent (preferably THF) with bromoacetonitrile to form compound (22). Nitrile (22) is reduced and cyclized to afford (23) as described in the literature (see Reddy, P. A.; Hsiang, B. C. H.; Latifi, T. N.; Hill, M. W.; Woodward K. E.; Rothman, S. M.; Ferrendelli, J. A.; Covey, D. F. J. Med. Chem. 1996, 39, 1898-1906). Compound (23) is treated with a base (preferably NaH) and is alkylated with (9) to form (24) as a mixture of cis/trans isomers that are separated by normal purification techniques.

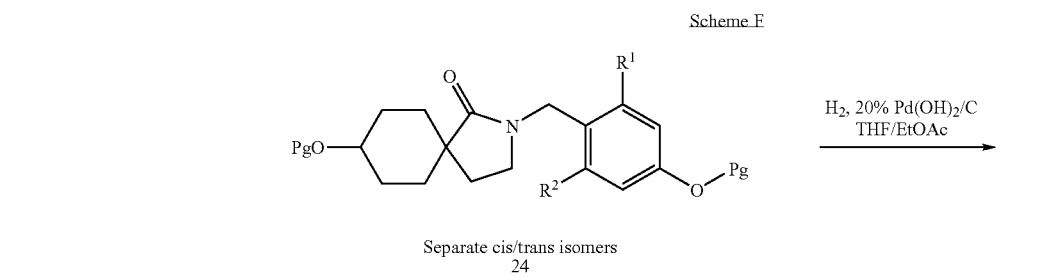

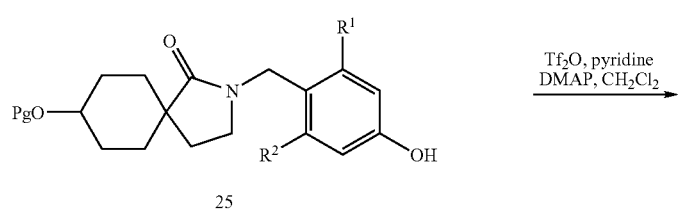

-continued
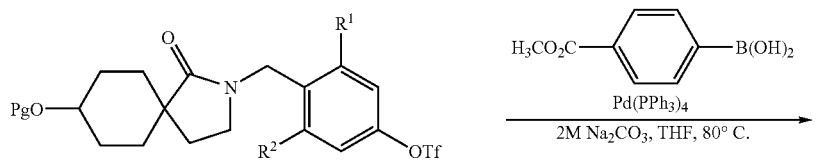
26
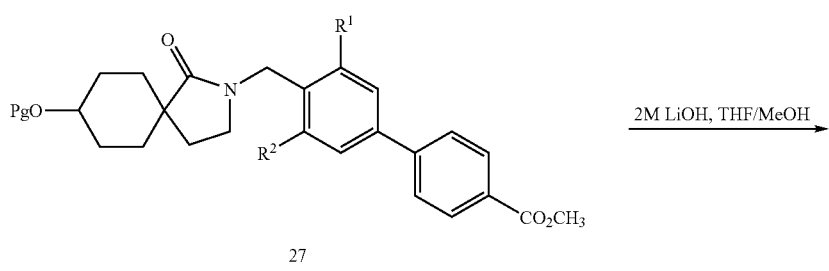
27
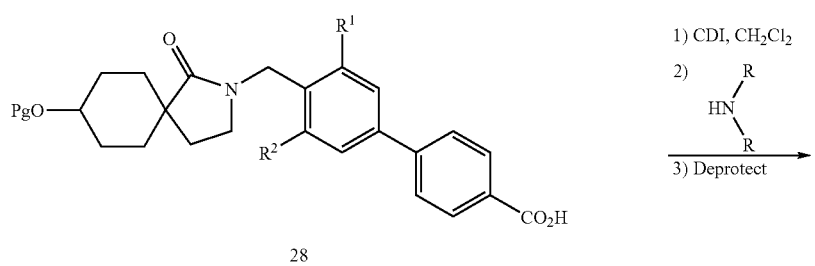
28
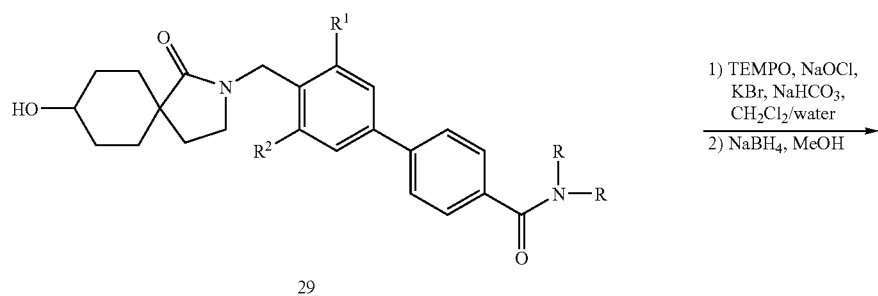
29
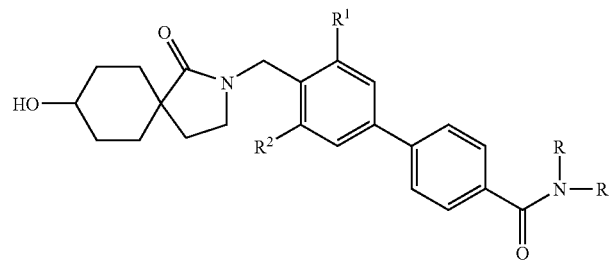
30

In Scheme F, compound (24) is deprotected by a suitable method, such as using hydrogen with a catalyst, to afford the phenol (25) which is reacted with triflic anhydride (trifluoromethanesulfonic anhydride) and a base, for example pyridine to prepare (26). A coupling reaction is performed on (26) using a phenylboronic acid reagent and a catalyst, such as palladium tetrakistriphenylphosphine to prepare ester (27). Hydrolysis of (27) affords the protected acid (28) which is coupled with an amine using standard amide coupling conditions such as 1,1'-carbonyldiimidazole to afford alcohol (29) after deprotection. The pure trans (or cis) alcohol (29) can be oxidized and reduced under standard conditions to produce a mixture of cis/trans alcohols (30) that are separated using standard purification techniques.

PREPARATION 1

3,5-dichloro-4-methylaniline

Dissolve 1,3-dichloro-2-methyl-5-nitrobenzene (0.50 g, 2.43 mmol) in DMF and treat with tin (II) chloride dihydrate (2.74 g, 12.1 mmol) in a single portion. Stir the reaction for 1 hour and dilute with ethyl acetate and filter through celite. Wash the filtrate four times with water and twice with brine, dry over MgSO$_4$, filter and concentrate to a dark oil. Purify the residue by silica gel chromatography eluting with a gradient of 5% to 10% ethyl acetate in hexanes to give 342 mg (80%) of the titled product as white flakes.

Scheme G

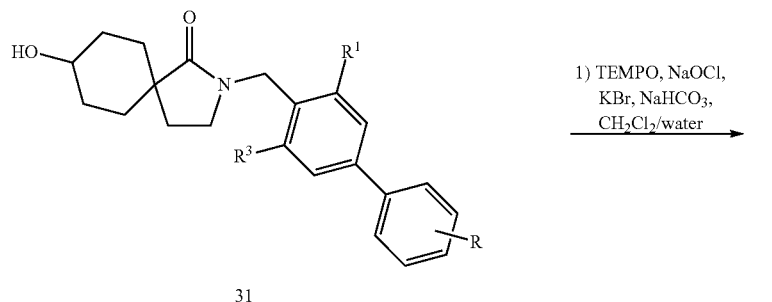

31

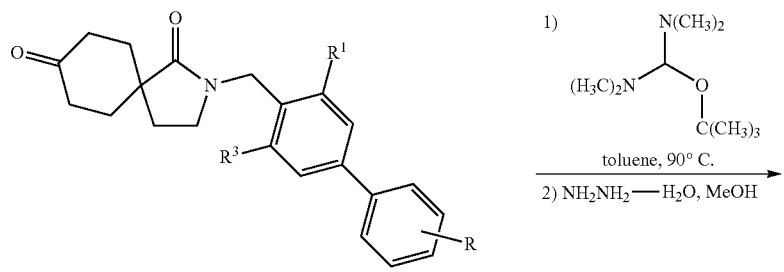

32

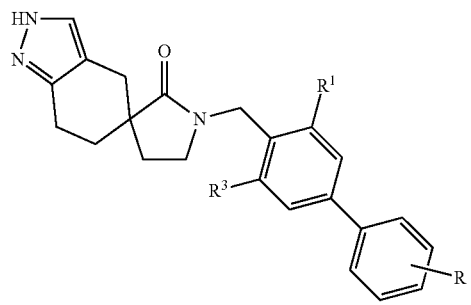

33

In Scheme G, compound (31) is oxidized using standard conditions such as TEMPO (2,2,6,6-tetramethyl-1-piperidinyloxy) and NaOCl to prepare ketone (32). Racemic pyrazole (33) is prepared by reacting ketone (32) stepwise with tert-butoxybis(dimethylamino)methane and then hydrazine hydrate. The pure enantiomers are separated by chiral HPLC purification.

PREPARATION 2

5-bromo-1,3-dichloro-2-methylbenzene

Suspend the 3,5-dichloro-4-methylaniline in 48% HBr (5 mL) and water (5 mL) and heat with a heat gun until the mixture is near the boiling point. Cool the slurry to room temperature and then cool to 0° C. with an ice/brine bath. Add a solution of sodium nitrite (109 mg, 1.58 mmol) in water (2 mL) dropwise. After the addition is complete, stir the reaction an additional 15 min in the cold bath. Add a solution of CuBr (1.08 g, 7.53 mmol) in 48% HBr (2 mL) and heat the rapidly stirring reaction to 50° C. for 1 hour. Cool the reaction to room temperature, dilute the reaction with ethyl acetate and discard the aqueous layer. Wash the organic layer with water and brine, dry with $MgSO_4$, filter through celite and concentrate to an orange residue. Purify the residue by silica gel chromatography eluting with hexanes to afford 164 mg (45%) of the product as a yellow solid.

PREPARATION 3

5-bromo-2-(bromomethyl)-1,3-dichlorobenzene

Heat a solution of 5-bromo-1,3-dichloro-2-methylbenzene (97 mg, 0.40 mmol), N-bromosuccinimide (76 mg, 0.425 mmol) and benzoyl peroxide (16 mg, 0.06 mmol) in $CCl_4$ (5 mL) to reflux for 3 hours under $N_2$. Cool the reaction to room temperature and concentrate to an orange residue. Purify the residue by silica gel chromatography eluting with hexanes to afford 112 mg (87%) of the product as white crystals.

PREPARATION 4

Tert-butyl-(3,5-dichloro-phenoxy)-dimethyl-silane

Dissolve 3,5 dichlorophenol (1 kg, 6.13 mol) in 3 L dimethylformamide and cool to 0° C. Add imidazole (918.74 g, 6.75 mol), followed by tertbutyldimethylsilyl chloride (1017.13 g, 6.75 mol). Warm the mixture to room temperature and stir for 15 min. Pour into water (6 L) and extract with ether (4 L). Wash the organic layer with water 2 times, 10% aqueous lithium chloride solution then brine before drying over sodium sulfate. Filter and concentrate under vacuum to 135 g of an oil.

PREPARATION 5

2,6-dichloro-4-hydroxy-benzaldehyde

Dissolve tert-butyl-(3,5-dichloro-phenoxy)-dimethyl-silane (425 g, 1.5 mol) in 4 L dry tetrahydrofuran and cool to −68° C. Slowly add 1.1 equivalents of sec-butyl lithium (103.1 g, 1.61 mol) at −68° C. (~1.75 hr). After addition is complete, stir the reaction at −70° C. for 30 min. Add dimethylformamide (168.5 g, 2.3 mol) and stir the reaction at −70° C. for 1 hr. Add 1 M hydrochloric acid in water (3.5 L) and allow the reaction to warm to room temperature. Pour the reaction mixture into ether (5 L), wash with water then brine. Dry over sodium sulfate and concentrate under vacuum to an orange solid. Triturate with cold dichloromethane and filter to recover 250 g (80%) pale yellow solid.

PREPARATION 6

2,6-dichloro-4-benzyloxy-benzaldehyde

Treat a mixture of 2,6-dichloro-4-hydroxy-benzaldehyde (250 g, 1.3 mol) and potassium carbonate (361.8 g, 2.62 mol) in 2 L dimethylformamide with benzyl bromide (268.64 g, 1.57 mol). Stir the reaction at room temperature for 1 hour. Filter off solids and pour into 12 L of water. Filter off solid, wash several times with water, air dry and dissolve in ethyl acetate. Dry over magnesium sulfate, filter and concentrate under vacuum to ~1.5 L. Allow to sit overnight then filter. Wash solid with minimal amount of hexane and vacuum dry. Concentrate the filtrate under vacuum and triturate with hexane to yield a second crop of product which when combined with the first crop equals 245 g white crystals. Repeat to obtain a third crop of 80 g as a light-tan powder (88% overall yield): $^1$H NMR (400 MHz, DMSO-$d_6$) δ 10.26 (s, 1H), 7.43 (m, 5H), 7.28 (s, 2H), 5.25 (s, 2H).

PREPARATION 7

(2,6-dichloro-4-benzyloxy-phenyl)-methanol

Treat a 0° C. mixture of 2,6-dichloro-4-benzyloxy-benzaldehyde (245 g, 0.871 mol) in ethanol (3 L) with sodium borohydride (32.97 g, 0.897 mol). Warm the reaction to room temperature and stir for 2 hours. Add the reaction mixture to saturated ammonium chloride (8 L). Extract the mixture with $CH_2Cl_2$ and dry the organic layer with $Na_2SO_4$. Remove the solvent in vacuo to afford 247 g (100%) of the titled product. $^1$H NMR (400 MHz, DMSO-$d_6$) δ 7.38 (m, 4H), 7.33 (m, 1H), 7.12 (s, 2H), 5.14 (s, 2H), 5.05 (t, 1H), 4.59 (d, 2H).

PREPARATION 8

2-bromomethyl-1,3-dichloro-5-benzyloxy-benzene

Treat a 0° C. solution of (2,6-dichloro-4-benzyloxy-phenyl)-methanol (247 g, 0.872 mol) in THF (2.5 L) with phosphorous tribromide (94.45 g, 0.35 mol) and stir for 30 minutes at 0° C. under $N_2$. Pour the reaction into saturated $NaHCO_3$ and extract twice with ethyl acetate. Dry the organic layer with $Na_2SO_4$ and remove the solvent in vacuo to afford 269 g (89%) of the titled product. ES MS (m/z): 346 (M+1).

PREPARATION 9

1-Cyanomethyl-cyclohexanecarboxylic acid methyl ester

Treat a −78° C. solution of methyl cyclohexane carboxylate (15.0 g, 0.105 mol) in THF (150 mL) with a 2M solution of lithium diisopropylamide in heptane/THF/ethylbenzene (63.3 mL, 0.126 mol) and stir at −78° C. for 20 minutes under $N_2$. Treat the reaction with bromoacetonitrile (25.31 g, 0.211 mol) and stir at −78° C. for 15 minutes. Warm the reaction to room temperature and stir 4 hours. Acidify the reaction with 1 N HCl and then dilute the reaction with ethyl acetate and wash with water. Dry the organic layer ($Na_2SO_4$) and remove the solvent in vacuo to afford crude product. Purify with a 0 to 30% ethyl acetate in hexanes gradient on silica gel to afford 7.78 g (41%) of the titled product. $R_f$=0.32 (3/1 hexanes/ethyl acetate).

PREPARATION 10

2-Aza-spiro[4.5]decan-1-one

A 0° C. mixture of 1-cyanomethyl-cyclohexanecarboxylic acid methyl ester (4.28 g, 23.6 mmol) and cobalt (II) chloride hexahydrate (2.81 g, 11.8 mmol) in THF (80 mL) and water (40 mL) is treated portion-wise with sodium borohydride (4.47 g, 0.118 mol) and is warmed to room temperature and stirred for 48 hours under $N_2$. The reaction is treated with 28% ammonium hydroxide (3.1 mL) and filtered through hyflo. The solvent is removed from the filtrate in vacuo and the residue is diluted with minimal water and brine and is extracted three times with 3:1 chloroform:isopropanol. The organic layer is dried (Na$_2$SO$_4$) and the solvent is removed in vacuo to afford crude product that is purified with a 0 to 10% methanol in CH$_2$Cl$_2$ gradient on silica gel to afford 1.95 g (54%) of the titled product. R$_f$=0.46 (9/1 CH$_2$Cl$_2$/methanol). MS (m/z): 154 (M+).

PREPARATION 11

1-(2-Fluoro-ethyl)-piperazine bis trifluoroacetic acid salt

Heat a mixture of 1-boc-piperazine (4.08 g, 21.9 mmol), 1-bromo-2-fluoroethane (16.68 g, 0.131 mol) and N,N-diisopropyl ethyl amine (17.0 g, 0.131 mol) in acetonitrile (40 mL) to 50° C. for 16 hours and then heat to reflux for 7 additional hours. Cool the reaction to room temperature and remove the solvent in vacuo. Treat the residue with 1 N NaOH (25 mL) and extract twice with ethyl acetate. Dry the organic layer with Na$_2$SO$_4$ and purify the crude product on silica with a 0 to 10% Methanol in CH$_2$Cl$_2$ gradient to afford 5.01 g (99%) of 4-(2-fluoro-ethyl)-piperazine-1-carboxylic acid tert-butyl ester (R$_f$ 0.36 (9/1 CH$_2$Cl$_2$/Methanol, I$_2$ stain).

Treat a solution of 4-(2-fluoro-ethyl)-piperazine-1-carboxylic acid tert-butyl ester (2.0 g, 8.62 mmol) in CH$_2$Cl$_2$ (20 mL) with TFA (10 mL) and stir at room temperature for 2 hours. Remove the solvent in vacuo to afford an oil and then add diethylether. A solid precipitates to give a slurry which is filtered under a cone of N$_2$. Dry on the filter to afford 2.73 g (88%) salt of the titled product. MS (m/z): 133 (M+).

PREPARATION 12

2-(4-Benzyloxy-2,6-dichloro-benzyl)-2-aza-spiro [4.5]decan-1-one

Treat a solution of 2-aza-spiro[4.5]decan-1-one (0.50 g, 3.26 mmol) in DMF (8 mL) with 60% sodium hydride (0.20 g, 5.0 mmol) and stir at room temperature for 20 minutes under N$_2$. Cool the reaction to 0° C., treat with 2-bromomethyl-1,3-dichloro-5-benzyloxy-benzene (1.24 g, 3.58 mmol), stir for 15 minutes at 0° C., warm to room temperature, and stir for 2 hours under N$_2$. Acidify the reaction with 1 N HCl, dilute the reaction with diethyl ether, and then wash with water. Dry the organic layer with Na$_2$SO$_4$ and remove the solvent in vacuo to afford crude product. Purify with a 0 to 100% ethyl acetate in hexanes gradient on silica gel to afford 1.23 g (90%) of the titled product. R$_f$=0.23 (3/1 ethyl acetate/hexanes). MS (m/z): 418 (M+).

PREPARATION 13

2-(2,6-Dichloro-4-hydroxy-benzyl)-2-aza-spiro[4.5] decan-1-one

Purge with N$_2$ and H$_2$ a mixture of 2-(4-benzyloxy-2,6-dichloro-benzyl)-2-aza-spiro[4.5]decan-1-one (1.18 g, 2.82 mmol) and 20% palladium (II) hydroxide on carbon (0.50 g) in ethyl acetate (100 mL) and stir under a balloon of H$_2$ for 4 hours at room temperature. Add sodium sulfate to the mixture and filter through hyflo. Remove the solvent in vacuo and purify the crude product on silica isocratically with 9:1 chloroform:methyl t-butyl ether on silica gel to afford 0.72 g (78%) of the titled product. R$_f$=0.18 (9:1 chloroform:methyl t-butyl ether).

PREPARATION 14

Trifluoro-methanesulfonic acid 3,5-dichloro-4-(1-oxo-2-aza-spiro[4.5]dec-2-ylmethyl)-phenyl ester Treat a 0° C. solution of 2-(2,6-dichloro-4-hydroxy-benzyl)-2-aza-spiro[4.5]decan-1-one (0.229 g, 0.38 mmol), pyridine (0.35 g, 4.42 mmol) and 4-dimethylaminopyridine (0.027 g, 0.22 mmol) in CH$_2$Cl$_2$ (20 mL) with trifluoromethanesulfonic anhydride (0.87 g, 3.08 mmol) and stir for 1 hour at 0° C. under N$_2$. Dilute the reaction with CH$_2$Cl$_2$ and wash with 1N HCl and water. Dry the organic layer with Na$_2$SO$_4$ and remove the solvent in vacuo to afford 0.83 g (82%) of the titled product. R$_f$=0.54 (1/1 hexanes/ethyl acetate). MS (m/z): 460 (M+).

PREPARATION 15

4-(tert-Butyl-diphenyl-silanyloxy)-cyclohexanecarboxylic acid ethyl ester

Treat a solution of cis/trans ethyl 4-hydroxycyclohexanecarboxylate (21.3 g, 0.124 mol) and imidazole (10.10 g, 0.148 mol) in DMF (150 mL) with t-butyl-diphenylsilyl chloride (37.39 g, 0.136 mol) and stir for 72 hours at room temperature. Dilute the reaction with diethyl ether and wash with 1N HCl and water. Dry the organic layer with Na$_2$SO$_4$ and remove the solvent in vacuo to afford crude product. Purify with a 0 to 20% ethyl acetate in hexanes gradient on silica gel to afford 40.4 g (80%) of the titled product. R$_f$=0.49 and 0.29 (5/1 hexanes/ethyl acetate).

PREPARATION 16

4-(tert-Butyl-diphenyl-silanyloxy)-1-cyanomethyl-cyclohexanecarboxylic acid ethyl ester Treat a −78° C. solution of 4-(tert-butyl-diphenyl-silanyloxy)-cyclohexanecarboxylic acid ethyl ester (21.22 g, 51.7 mmol) in THF (200 mL) with a 2M solution of lithium diisopropylamide in heptane/THF/ethylbenzene (31 mL, 62.0 mmol) and stir at −78° C. for 15 minutes under N$_2$. Warm the reaction to −20° C. and then re-cool to −78° C. Treat the reaction with bromoacetonitrile (9.30 g, 77.5 mmol) and stir at −78° C. for 1 hour. Warm the reaction to room temperature and stir 1 hour. Acidify the reaction with 1 N HCl, dilute with ethyl acetate, and wash with water. Dry the organic layer with Na$_2$SO$_4$ and remove the solvent in vacuo to afford crude product that is purified with a 0 to 20% ethyl acetate in hexanes gradient on silica gel to afford 10.96 g (47%) of the titled product. R$_f$=0.25 and 0.21 (5/1 hexanes/ethyl acetate). MS (m/z): 450 (M+).

PREPARATION 17

8-(tert-Butyl-diphenyl-silanyloxy)-2-aza-spiro[4.5] decan-1-one

Treat a 0° C. mixture of 4-(tert-butyl-diphenyl-silanyloxy)-1-cyanomethyl-cyclohexanecarboxylic acid ethyl ester (7.19 g, 15.9 mmol), cobalt (II) chloride hexahydrate (1.90 g, 7.98 mmol) in THF (130 mL), and water (65 mL) portionwise with sodium borohydride (3.02 g, 7.98 mmol). Warm to room temperature and stir for 16 hours under N$_2$. Heat the reaction to 50° C. for 8 hours, cool to room temperature and stir 16 hours under N$_2$. Treat the reaction with 28% ammonium hydroxide (2 mL) and filter through hyflo. Remove the solvent from the filtrate in vacuo and dilute the residue with minimal water and brine and extract three times with 3:1 chloroform:isopropanol. Dry the organic layer with $Na_2SO_4$ and remove the solvent in vacuo to afford crude product. Purify with a 0 to 10% methanol in $CH_2Cl_2$ gradient on silica gel to afford 1.20 g (18%) of the titled product. $R_f$=0.48 and 0.61 (9/1 $CH_2Cl_2$/methanol). MS (m/z): 408 (M+).

PREPARATION 18 cis/trans 2-(4-Benzyloxy-2,6-dichloro-benzyl)-8-(tert-butyl-diphenyl-silanyloxy)-2-aza-spiro[4.5]decan-1-one Treat a solution of 8-(tert-butyl-diphenyl-silanyloxy)-2-aza-spiro[4.5]decan-1-one (2.37 g, 5.81 mmol) in DMF (25 mL) with 60% sodium hydride (0.35 g, 8.72 mmol) and stir at room temperature for 15 minutes under $N_2$. Cool the reaction to 0° C., treat with 5-benzyloxy-2-bromomethyl-1,3-dichloro-benzene (2.21 g, 6.39 mmol), stir for 15 minutes at 0° C., warm to room temperature, and stir for 4 hours under $N_2$. Acidify the reaction with 1 N HCl. Dilute the reaction with diethyl ether and wash with water. Dry the organic layer with $Na_2SO_4$ and remove the solvent in vacuo to afford crude product. Purify with a 0 to 20% ethyl acetate in hexanes gradient on silica gel to afford 2.96 g of isomer 1 (cis) $R_f$=0.46 (3/1 ethyl acetate/hexanes) and 0.236 g of isomer 2 (trans) $R_f$=0.37 (3/1 ethyl acetate/hexanes). MS (m/z): 672 (M+).

PREPARATION 19 trans 8-(tert-Butyl-diphenyl-silanyloxy)-2-(2,6-dichloro-4-hydroxy-benzyl)-2-aza-spiro[4.5]decan-1-one Purge with $N_2$ and $H_2$ a mixture of isomer 2 (trans) 2-(4-benzyloxy-2,6-dichloro-benzyl)-8-(tert-butyl-diphenyl-silanyloxy)-2-aza-spiro[4.5]decan-1-one (0.236 g, 0.35 mmol) and 20% palladium (II) hydroxide on carbon (50 mg) in THF (25 mL) and ethyl acetate (5 mL) and stir under a balloon of $H_2$ for 16 hours at room temperature. Add sodium sulfate to the mixture and filter through hyflo. Remove the solvent in vacuo from the filtrate to afford 0.229 g (100%) of the titled product. $R_f$=0.22 (1/1 ethyl acetate/hexanes).

PREPARATION 20

Trifluoro-methanesulfonic acid trans 4-[8-(tert-butyl-diphenyl-silanyloxy)-1-oxo-2-aza-spiro[4.5]dec-2-ylmethyl]-3,5-dichloro-phenyl ester Treat a 0° C. solution of 8-(tert-butyl-diphenyl-silanyloxy)-2-(2,6-dichloro-4-hydroxy-benzyl)-2-aza-spiro[4.5]decan-1-one (0.229 g, 0.38 mmol), pyridine (0.061 g, 0.77 mmol) and 4-dimethylaminopyridine (0.005 g, 0.041 mmol) in $CH_2Cl_2$ (25 mL) with trifluoromethanesulfonic anhydride (0.167 g, 0.59 mmol) and stir for 1 hour at 0° C. under $N_2$. Dilute the reaction with $CH_2Cl_2$ and wash with 1N HCl and water. Dry the organic layer with $Na_2SO_4$ and remove the solvent in vacuo to afford 0.230 g (82%) of the titled product. $R_f$=0.29 (3/1 hexanes/ethyl acetate).

PREPARATION 21 trans 4'-[8-(tert-Butyl-diphenyl-silanyloxy)-1-oxo-2-aza-spiro[4.5]dec-2-ylmethyl]-3',5'-dichloro-biphenyl-4-carboxylic acid methyl ester Purge with $N_2$ a mixture of trifluoro-methanesulfonic acid 4-[8-(tert-butyl-diphenyl-silanyloxy)-1-oxo-2-aza-spiro[4.5]dec-2-ylmethyl]-3,5-dichloro-phenyl ester (0.23 g, 0.31 mmol) and 4-methoxycarbonyl phenylboronic acid (0.068 g, 0.38 mmol) in THF (5 mL) and 2M sodium carbonate (0.5 mL). Treat the reaction with $Pd(PPh_3)_4$ (0.018 g, 0.015 mmol) and heat to 80° C. for 90 minutes under $N_2$. Cool the reaction, dilute with ethyl acetate, and wash with 1N HCl and water. Dry the organic layer with $Na_2SO_4$ and remove the solvent in vacuo to afford crude product. Purify with a 0 to 100% ethyl acetate in hexanes gradient on silica gel to afford 0.22 g (100%) of the titled product. $R_f$=0.20 (3/1 hexanes/ethyl acetate). MS (m/z): 700 (M+).

PREPARATION 22 trans 4'-[8-(tert-Butyl-diphenyl-silanyloxy)-1-oxo-2-aza-spiro[4.5]dec-2-ylmethyl]-3',5'-dichloro-biphenyl-4-carboxylic acid Treat a mixture Preparation 21 (0.22 g, 0.31 mmol) in THF (5 mL) and methanol (0.5 mL) with 2M lithium hydroxide (0.8 mL) and stir for 16 hours at room temperature. Dilute the reaction with ethyl acetate and wash with 1N HCl and water. Dry the organic layer with $Na_2SO_4$ and remove the solvent in vacuo to afford 0.185 g (86%) of the titled product. $R_f$=0.11 (1/1 hexanes/ethyl acetate). MS (m/z): 700 (M+).

PREPARATION 23 trans 8-(tert-Butyl-diphenyl-silanyloxy)-2-[3,5-dichloro-4'-(4-trifluoromethyl-piperidine-1-carbonyl)-biphenyl-4-ylmethyl]-2-aza-spiro[4.5]decan-1-one Treat a solution of Preparation 22 (0.183 g, 0.27 mmol) in $CH_2Cl_2$ (8 mL) with 1,1'-carbonyldiimidazole (0.069 g, 0.43 mmol) and stir for 1 hour at room temperature under $N_2$. Then, treat the reaction with 4-(trifluoromethyl)piperidine HCl (0.101 g, 0.53 mmol) and diisopropylethylamine (0.14 g, 1.09 mmol) and stir for 16 hours at room temperature under $N_2$. Dilute the reaction with ethyl acetate and wash with 1N HCl and water. Dry the organic layer with $Na_2SO_4$ and remove the solvent in vacuo to afford crude product. Purify with a 0 to 100% ethyl acetate in hexanes gradient on silica gel to afford 0.19 g (87%) of the titled product. $R_f$=0.26 (1/1 hexanes/ethyl acetate). MS (m/z): 821 (M+).

PREPARATION 24

2-[3,5-Dichloro-4'-(4,4-difluoro-piperidine-1-carbonyl)-biphenyl-4-ylmethyl]-2-aza-spiro[4.5]decane-1,8-dione Combine a solution of cis-[3,5-dichloro-4'-(4,4-difluoro-piperidine-1-carbonyl)-biphenyl-4-ylmethyl]-8-hydroxy-2-aza-spiro[4.5]decan-1-one (0.582 g, 1.06 mmol) and 2,2,6,6-tetramethyl-1-piperidinyloxy (TEMPO) (0.013 g, 0.083 mmol) in $CH_2Cl_2$ (30 mL) with a solution of potassium bromide (0.010 g, 0.083 mmol) in water (5 mL) and cool to 0° C. Add a solution of 5.25% NaOCl (3 mL) and $NaHCO_3$ (0.133 g, 1.58 mmol) to the 0° C. reaction mixture and stir for 30 minutes. Dilute the reaction with ethyl acetate and wash with water. Dry the organic layer with $Na_2SO_4$ and remove the solvent in vacuo to afford 0.5479 g (94%) of the titled product. $R_f$=0.43 (100% ethyl acetate). MS (m/z): 549 (M+).

PREPARATION 25 cis 8-(tert-Butyl-diphenyl-silanyloxy)-2-(3,5-dichloro-4'-fluoro-biphenyl-4-ylmethyl)-2-aza-spiro[4.5]decan-1-one Purge with $N_2$ a mixture of trifluoro-methanesulfonic acid 4-[8-(tert-butyl-diphenyl-silanyloxy)-1-oxo-2-aza-spiro[4.5]dec-2-ylmethyl]-3,5-dichloro-phenyl ester (1.19 g, 1.63 mmol) and 4-fluorophenylboronic acid (0.27 g, 1.93 mmol) in THF (24 mL) and 2M sodium carbonate (2.4 mL). Treat the reaction with $Pd(PPh_3)_4$ (0.094 g, 0.081 mmol) and heat to 80° C. for 90 minutes under $N_2$. Cool the reaction and dilute with ethyl acetate and wash with 1N HCl and water. Dry the organic layer with $Na_2SO_4$ and remove the solvent in vacuo to afford crude product. Purify with a 0 to 100% ethyl acetate in hexanes gradient on silica gel to afford 0.81 g (76%) of the titled product. $R_f$=0.47 (3/1 hexanes/ethyl acetate). MS (m/z): 700 (M+).

PREPARATION 26

2-[3,5-Dichloro-4'-(4-trifluoromethyl-piperidine-1-carbonyl)-biphenyl-4-ylmethyl]-2-aza-spiro[4.5]decane-1,8-dione A solution of cis 2-[3,5-dichloro-4'-(4-trifluoromethyl-piperidine-1-carbonyl)-biphenyl-4-ylmethyl]-8-hydroxy-2-aza-spiro[4.5]decan-1-one (0.232 g, 0.39 mmol) and 2,2,6,6-tetramethyl-1-piperidinyloxy (TEMPO) (0.005 g, 0.032 mmol) in $CH_2Cl_2$ (12 mL) is combined with a solution of potassium bromide (0.004 g, 0.033 mmol) in water (2 mL) and cooled to 0° C. A solution of 5.25% NaOCl (1.13 mL) and $NaHCO_3$ (0.050 g, 0.59 mmol) is prepared and added to the 0° C. reaction mixture and the resultant mixture is stirred for 30 minutes. The reaction is diluted with ethyl acetate and washed with water. The organic layer is dried ($Na_2SO_4$) and the solvent is removed in vacuo to afford crude product that is purified with silica using a 50 to 100% gradient of ethyl acetate in hexanes on silica gel to afford 0.191 g (83%) of the titled product. $R_f$=0.32 (100% ethyl acetate). MS (m/z): 549 (M+).

EXAMPLE 1

2-(4-Bromo-2,6-dichloro-benzyl)-2-aza-spiro[4.5]decan-1-one

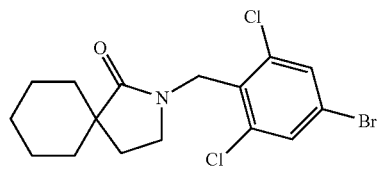

Treat a solution of 2-aza-spiro[4.5]decan-1-one (0.138 g, 0.901 mmol) in DMF (5 mL) with 60% sodium hydride (0.054 g, 1.35 mmol) and stir at room temperature for 15 minutes under $N_2$. Cool the reaction to 0° C., treat with 5-bromo-2-(bromomethyl)-1,3-dichlorobenzene (0.316 g, 0.991 mmol), and stir for 15 minutes at 0° C. Warm to room temperature and stir for 2 hours under $N_2$. Acidify the reaction with 1 N HCl. Dilute with diethyl ether and wash with water. Dry the organic layer with $Na_2SO_4$ and remove the solvent in vacuo to afford crude product. Purify with a 0 to 100% ethyl acetate in hexanes gradient on silica gel to afford 0.258 g (73%) of the titled product. $R_f$=0.24 (3/1 ethyl acetate/hexanes). MS (m/z): 392 (M+).

EXAMPLE 2

2-(3,5-Dichloro-4'-fluoro-biphenyl-4-ylmethyl)-2-aza-spiro[4.5]decan-1-one

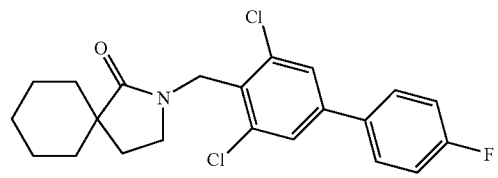

Purged with $N_2$ a mixture of 2-(4-bromo-2,6-dichloro-benzyl)-2-aza-spiro[4.5]decan-1-one (0.091 g, 0.23 mmol) and 4-fluorophenylboronic acid (0.097 g, 0.69 mmol) in toluene (6 mL) and 2M sodium carbonate (0.8 mL). Treat the reaction with $Pd(PPh_3)_4$ (0.013 g, 0.011 mmol) and heat to 90° C. for 2 hours under $N_2$. Cool the reaction and dilute with ethyl acetate, and then wash with 1N HCl and water. Dry the organic layer with $Na_2SO_4$ and remove the solvent in vacuo to afford crude product. Purify with a 0 to 100% ethyl acetate in hexanes gradient on silica gel to afford 0.096 g (100%) of the titled product. $R_f$=0.25 (3/1 hexanes/ethyl acetate). MS (m/z): 406 (M+).

EXAMPLE 3

3',5'-Dichloro-4'-(1-oxo-2-aza-spiro[4.5]dec-2-ylmethyl)-biphenyl-4-carboxylic acid methyl ester

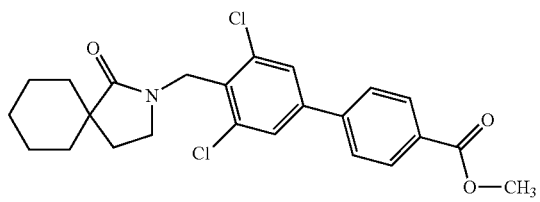

Purge with $N_2$ a mixture of 2-(4-bromo-2,6-dichloro-benzyl)-2-aza-spiro[4.5]decan-1-one (0.14 g, 0.36 mmol) and 4-methoxycarbonyl phenylboronic acid (0.19 g, 1.05 mmol) in toluene (10 mL) and 2M sodium carbonate (1.25 mL). Treat the reaction with $Pd(PPh_3)_4$ (0.041 g, 0.035 mmol) and heat to 90° C. for 4 hours under $N_2$. Cool the reaction and dilute with ethyl acetate, and then wash with 1N HCl and water. Dry the organic layer with $Na_2SO_4$ and remove the solvent in vacuo to afford crude product. Purify with a 0 to 100% ethyl acetate in hexanes gradient on silica gel to afford 0.102 g (64%) of the titled product. $R_f$=0.51 (1/1 hexanes/ethyl acetate). MS (m/z): 446

EXAMPLE 4

3',5'-Dichloro-4'-(1-oxo-2-aza-spiro[4.5]dec-2-ylmethyl)-biphenyl-4-carboxylic acid

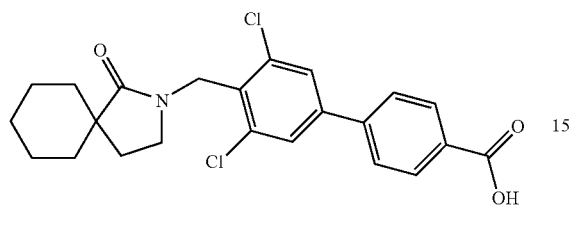

Treat a solution of Example 3 (0.087 g, 0.19 mmol) in methanol (10 mL) with 5N NaOH (0.60 mL) and stir at room temperature for 16 hours. Remove the solvent in vacuo to give a residue that is acidified with 1N HCl. Dilute the mixture with ethyl acetate and wash with water. Dry the organic layer with $Na_2SO_4$ and remove the solvent in vacuo to afford 0.086 g (100%) of the titled product. MS (m/z): 432 (M+).

EXAMPLE 5

2-[3,5-Dichloro-4'-(4-trifluoromethyl-piperidine-1-carbonyl)-biphenyl-4-ylmethyl]-2-aza-spiro[4.5]decan-1-one

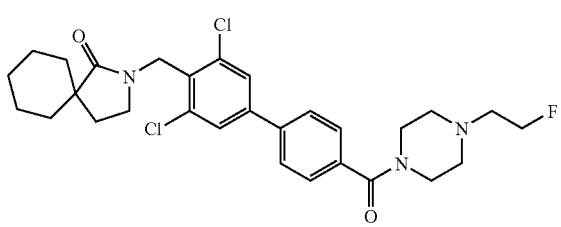

Treat a solution of Example 4 (0.079 g, 0.18 mmol) in $CH_2Cl_2$ (8 mL) with 1,1'-carbonyldiimidazole (0.047 g, 0.29 mmol) and stir for 1 hour at room temperature under $N_2$. Then, treat the reaction with 4-(trifluoromethyl)piperidine HCl (0.087 g, 0.46 mmol) and diisopropylethylamine (0.12 g, 0.92 mmol) and stir for 16 hours at room temperature under $N_2$. Dilute the reaction with ethyl acetate and wash with 1N HCl and water. Dry the organic layer with $Na_2SO_4$ and remove the solvent in vacuo to afford crude product. Purify on silica with a 0 to 10% methanol in $CH_2Cl_2$ gradient on silica gel and then isocratically with 50/50 ethyl acetate/hexanes gradient on silica gel to afford 0.067 g (64%) of the titled product. $R_f$=0.68 (9/1 $CH_2Cl_2$/methanol). MS (m/z): 567 (M+).

EXAMPLE 6

2-{3,5-Dichloro-4'-[4-(2-fluoro-ethyl)-piperazine-1-carbonyl]-biphenyl-4-ylmethyl}-2-aza-spiro[4.5]decan-1-one

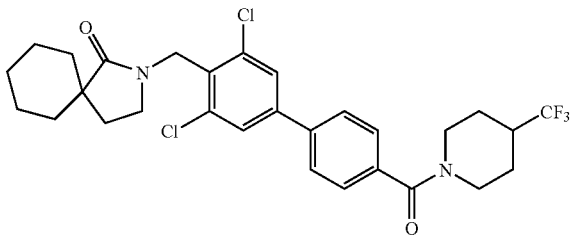

Prepare Example 6 essentially by the method described in Example 5 using Example 4 and 1-(2-fluoro-ethyl)-piperazine bis trifluoroacetic acid salt. Purification on silica gel affords 0.153 g of the titled product. $R_f$=0.42 (9:1 $CH_2Cl_2$:methanol). MS (m/z): 546 (M+).

EXAMPLE 7

2-(2,6-Dichloro-4-morpholin-4-yl-benzyl)-2-aza-spiro[4.5]decan-1-one

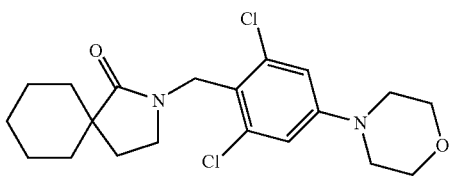

Heat a solution of trifluoro-methanesulfonic acid 3,5-dichloro-4-(1-oxo-2-aza-spiro[4.5]dec-2-ylmethyl)-phenyl ester (0.15 g, 0.32 mmol) and morpholine (0.099 g, 1.13 mmol) in 1-methyl-2-pyrrolidine (2.5 mL) to 201° C. for 1.5 hours in a microwave reactor. Cool the reaction to room temperature and treat with 2M LiOH (1 mL) and stir 16 hours at room temperature. Dilute the reaction with ethyl acetate and wash with water. Dry the organic layer with $Na_2SO_4$ and remove the solvent in vacuo to afford crude product. Purify on silica isocratically using 5% methyl t-butyl ether in chloroform to afford 0.064 g (50%) of the titled product. $R_f$=0.22 (9:1 chloroform:methyl t-butyl ether). MS (m/z): 397 (M+).

EXAMPLE 8 trans 2-[3,5-Dichloro-4'-(4-trifluoromethyl-piperidine-1-carbonyl)-biphenyl-4-ylmethyl]-8-hydroxy-2-aza-spiro[4.5]decan-1-one

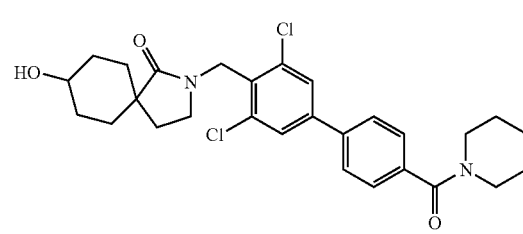

Treat a mixture of 8-(tert-butyl-diphenyl-silanyloxy)-2-[3,5-dichloro-4'-(4-trifluoromethyl-piperidine-1-carbonyl)-biphenyl-4-ylmethyl]-2-aza-spiro[4.5]decan-1-one (0.19 g, 0.23 mmol) in THF (6 mL) and water (3 mL) with trifluoroacetic acid (2 mL) and heat to reflux and stir for 2 hours under $N_2$. Cool the reaction and dilute with ethyl acetate and wash with water and saturated $NaHCO_3$. Dry the organic layer with $Na_2SO_4$ and remove the solvent in vacuo to afford crude product. Purify with a 50 to 100% ethyl acetate in hexanes gradient on silica gel to afford 0.89 g (57%) of the titled product. $R_f$=0.09 (100% ethyl acetate). MS (m/z): 583 (M+).

EXAMPLE 9 cis 2-[3,5-Dichloro-4'-(4-trifluoromethyl-piperidine-1-carbonyl)-biphenyl-4-ylmethyl]-8-hydroxy-2-aza-spiro[4.5]decan-1-one

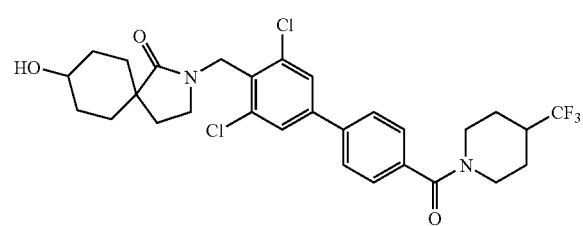

Prepare Example 9 essentially by the method described in Example 8 using isomer 1 (cis) 2-(4-benzyloxy-2,6-dichloro-benzyl)-8-(tert-butyl-diphenyl-silanyloxy)-2-aza-spiro[4.5] decan-1-one which affords 0.185 g of the titled product. $R_f$=0.15 (100% ethyl acetate). MS (m/z): 583 (M+).

EXAMPLE 10 cis -[3,5-Dichloro-4'-(4,4-difluoro-piperidine-1-carbonyl)-biphenyl-4-ylmethyl]-8-hydroxy-2-aza-spiro[4.5]decan-1-one

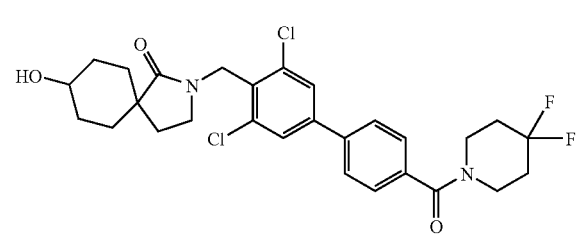

Prepare Example 10 essentially by the method described in Example 8 using isomer 1 (cis) 2-(4-benzyloxy-2,6-dichloro-benzyl)-8-(tert-butyl-diphenyl-silanyloxy)-2-aza-spiro[4.5]decan-1-one and 4,4-difluoropiperidin HCl. Purification on silica gel affords 0.64 g of the titled product. $R_f$=0.14 (100% ethyl acetate). MS (m/z): 551 (M+).

EXAMPLE 11 trans-[3,5-Dichloro-4'-(4,4-difluoro-piperidine-1-carbonyl)-biphenyl-4-ylmethyl]-8-hydroxy-2-aza-spiro[4.5]decan-1-one

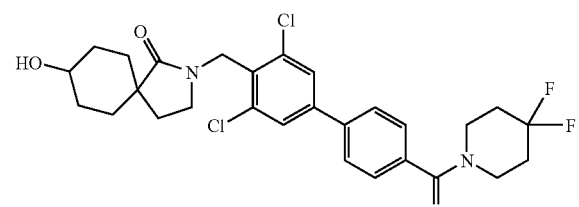

Treat a 0° C. solution of 2-[3,5-dichloro-4'-(4,4-difluoro-piperidine-1-carbonyl)-biphenyl-4-ylmethyl]-2-aza-spiro[4.5]decane-1,8-dione (0.386 g, 0.70 mmol) in methanol (10 mL) with sodium borohydride (0.040 g, 1.06 mmol) and stir for 30 minutes at 0° C. Acidify the reaction with 1N HCl, dilute with ethyl acetate and wash with water. Dry the organic layer with $Na_2SO_4$ and remove the solvent in vacuo to afford a mixture of cis:trans isomers. Purify on silica using a 50 to 100% gradient of ethyl acetate in hexanes on silica gel to afford 0.073 g (19%) of the titled product. $R_f$=0.13 (100% ethyl acetate). MS (m/z): 551 (M+).

EXAMPLE 12 cis 2-(3,5-Dichloro-4'-fluoro-biphenyl-4-ylmethyl)-8-hydroxy-2-aza-spiro[4.5]decan-1-one

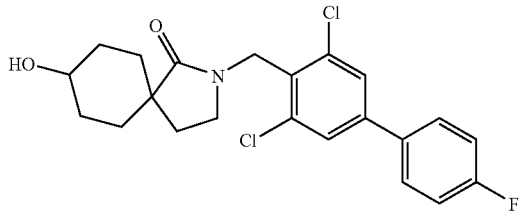

Prepare Example 12 essentially by the method described in Example 8 using 8-(tert-butyl-diphenyl-silanyloxy)-2-(3,5-dichloro-4'-fluoro-biphenyl-4-ylmethyl)-2-aza-spiro[4.5]decan-1-one which affords 0.44 g of the titled product. $R_f$=0.22 (100% ethyl acetate). MS (m/z): 422 (M+).

EXAMPLE 13

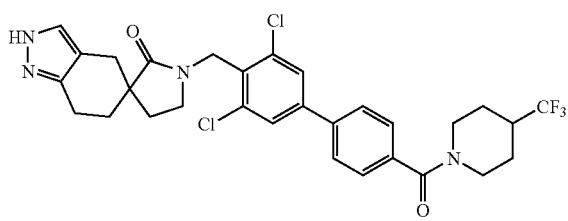

Treat a solution of 2-[3,5-dichloro-4'-(4-trifluoromethyl-piperidine-1-carbonyl)-biphenyl-4-ylmethyl]-2-aza-spiro[4.5]decane-1,8-dione (0.160 g, 0.27 mmol) in toluene (4 mL) with tert-butoxybis(dimethylamino)methane (0.062 g, 0.36 mmol) and heat to 90° C. and stir for 2.5 hours under $N_2$. Cool the reaction, remove the solvent in vacuo to afford an oil, and dissolve the oil in methanol (3 mL). Add hydrazine hydrate (0.015 g, 0.31 mmol) and stir the reaction at room temperature for 16 hours under $N_2$. Remove the solvent in vacuo to afford an oil and then dissolve in ethyl acetate. Extract the organic layer with water, dry with $Na_2SO_4$, and remove the solvent to afford crude product. Purify with silica gel using a 0 to 10% gradient of methanol in $CH_2Cl_2$ to afford 0.109 g (66%) of the titled product. $R_f$=0.40 (9/1 $CH_2Cl_2$/methanol). MS (m/z): 605 (M+).

EXAMPLE 14

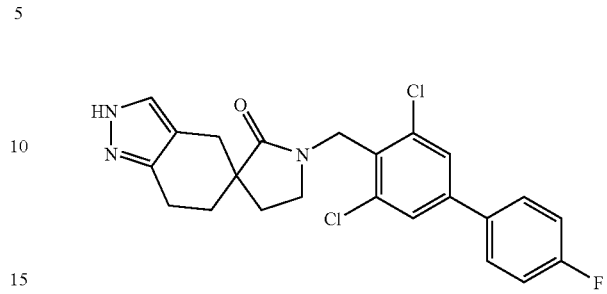

Prepare Example 14 essentially by the method described in Example 13 using cis-2-(3,5-dichloro-4'-fluoro-biphenyl-4-ylmethyl)-8-hydroxy-2-aza-spiro[4.5]decan-1-one which affords 0.319 g of the titled product. $R_f$=0.39 (9/1 $CH_2Cl_2$/methanol). MS (m/z): 444 (M+).

EXAMPLES 15 AND 16

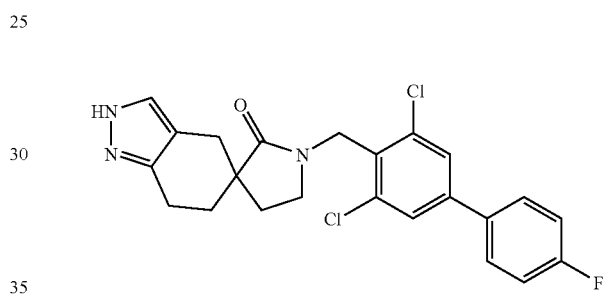

Separate Example 14 into the enantiomers by chiral HPLC (Chiralcel OD 8×35 cm column, isocratic 50:50 3A ethanol:heptane with 0.2% dimethylethylamine, 400 mL/min, UV 260 nm) to afford 120 mg of enantiomer 1 (97.0% ee) and 96 mg of enantiomer 2 (95.6% ee). Analytical HPLC: Chiralcel OD-H 4.6×150 mm column, isocratic 50:50 3A ethanol:heptane with 0.2% dimethylethylamine, 0.6 mL/min, UV 250 nm, isomer 1 elutes 5.5 minutes, isomer 2 elutes 6.6 minutes. ES MS (m/z): 444 (M+).
Example 15=Isomer 1.
Example 16=Isomer 2.

EXAMPLES 17 AND 18

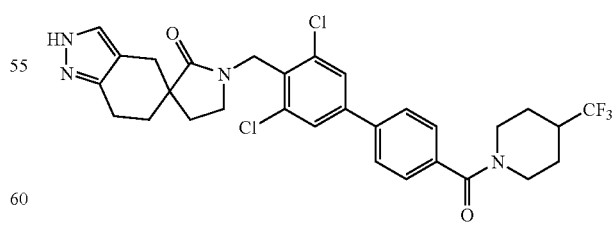

Separate Example 13 into the enantiomers by chiral HPLC (Chiralpak AD 5×33 cm column, isocratic 60:40 3A ethanol:heptane with 0.2% dimethylethylamine, 150 mL/min, UV 270 nm) to afford 32 mg of enantiomer 1 (>99% ee) and 28 mg of enantiomer 2 (98.2% ee). Analytical HPLC: Chiralpak AD-H 4.6×150 mm column, isocratic 60:40 3A ethanol:heptane with 0.2% dimethylethylamine, 0.6 mL/min, UV 270 nm, isomer 1 elutes 11.6 minutes, isomer 2 elutes 14.7 minutes. ES MS (m/z): 605 (M+).

Example 17=Isomer 1.
Example 18=Isomer 2.

In the following section enzyme and functional assays are described which are useful for evaluating the compounds of the invention.

each plate individually from the stacker and places them in position for addition of 5 μL/well of a 250 μM carbenoxolone solution to stop the enzymatic reaction. Plates are then shaken once more for 15 seconds then placed into an Ultra 384 microplate reader (355EX/460EM) for detection of NADPH fluorescence.

Data for example compounds in the 11-βHSD1 assay are shown below:

| Example | Structure | Human 11-βHSD1 $IC_{50}$ (nM) |
|---|---|---|
| 6 | 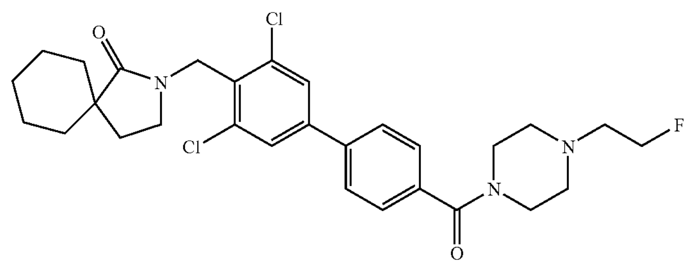 | 888 |
| 14 | 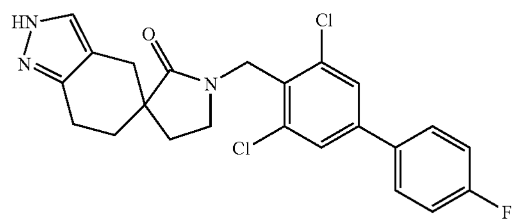 | 552 |

11β-HSD Type 1 Enzyme Assay

Human 11β-HSD type 1 activity is measured by assaying NADPH production by fluorescence assay. Solid compounds are dissolved in DMSO to a concentration of 10 mM. Twenty microliters of each are then transferred to a column of a 96-well polypropylene Nunc plate where they are further diluted 50-fold followed by subsequent two-fold titration, ten times across the plate with additional DMSO using a Tecan Genesis 200 automated system. Plates are then transferred to a Tecan Freedom 200 system with an attached Tecan Temo 96-well head and an Ultra 384 plate reader. Reagents are supplied in 96-well polypropylene Nunc plates and are dispensed individually into black 96-well Molecular Devices High Efficiency assay plates (40 μL/well capacity) in the following fashion: 9 μL/well of substrate (2.22 mM NADP, 55.5 μM Cortisol, 10 mM Tris, 0.25% Prionex, 0.1% Triton X100), 3 μL/well of water to compound wells or 3 μL to control and standard wells, 6 μL/well recombinant human 11β-HSD type 1 enzyme, 2 μL/well of compound dilutions. For ultimate calculation of percent inhibition, a series of wells are added that represent assay minimum and maximum: one set containing substrate with 667 μM carbenoxolone (background), and another set containing substrate and enzyme without compound (maximum signal). Final DMSO concentration is 0.5% for all compounds, controls and standards. Plates are then placed on a shaker by the robotic arm of the Tecan for 15 seconds before being covered and stacked for a three hour incubation period at room temperature. Upon completion of this incubation, the Tecan robotic arm removes Compounds of the invention can also tested for selectivity against 11-βHSD2 in an assay similar to that described for 11-βHSD1, but using the 11-βHSD2 enzyme. The assay using the 11-βHSD2 enzyme can be carried out by the methods described herein and supplemented by methods known in the art.

Human Aortic Smooth Muscle Cell Assay

Primary human aortic smooth muscle cells (AoSMC) are cultured in 5% FBS growth medium to a passage number of 6, then pelleted by centrifugation and resuspended at a density of $9 \times 10^4$ cells/mL in 0.5% FBS assay medium containing 12 ng/mL hTNFα to induce expression of 11β-HSD1. Cells are seeded into 96-well tissue culture assay plates at 100 μL/well ($9 \times 10^3$ cells/well) and incubated for 48 hours at 37° C., 5% $CO_2$. Following induction, cells are incubated for 4 hours at 37° C., 5% $CO_2$ in assay medium containing test compounds then treated with 10 μL/well of 10 μM cortisone solubilized in assay medium, and incubated for 16 hours at 37° C., 5% $CO_2$. Medium from each well is transferred to a plate for subsequent analysis of cortisol using a competitive fluorescence resonance time resolved immunoassay. In solution, an allophycocyanin (APC)-cortisol conjugate and free cortisol analyte compete for binding to a mouse anti-cortisol antibody/Europium (Eu)-anti mouse IgG complex. Higher levels of free cortisol result in diminishing energy transfer from the Europium-IgG to the APC-cortisol complex resulting in less APC fluorescence. Fluorescent intensities for Europium and APC are measured using a LJL Analyst AD. Europium and APC excitation is measured using 360 nm excitation and 615 nm and 650 nm emission filters respectively. Time resolved parameters for Europium were 1000 µs integration time with a 200 µs delay. APC parameters are set at 150 µs integration time with a 50 µs delay. Fluorescent intensities measured for APC are modified by dividing by the Eu fluorescence (APC/Eu). This ratio is then used to determine the unknown cortisol concentration by interpolation using a cortisol standard curve fitted with a 4-parameter logistic equation. These concentrations are then used to determine compound activity by plotting concentration versus % inhibition, fitting with a 4-parameter curve and reporting the $IC_{50}$.

All of the examples disclosed herein demonstrate activity in the human aortic smooth muscle cell assay with $IC_{50}$ of less than 500 nM. Preferred examples demonstrate activity in the human aortic smooth muscle cell assay with $IC_{50}$ of less than 300 nM. Data for example compounds in the human aortic smooth muscle cell assay are shown below:

average weight of 25 grams. Exact weights are taken upon arrival and the mice randomized into groups of similar weights. Compounds are prepared in 1% w-w HEC, 0.25% w-w polysorbate 80, 0.05% w-w Dow Corning antifoam #1510-US at various doses based on assumed average weight of 25 grams. Compounds are dosed orally, 200 µl per animal, followed by a subcutaneous dose, 200 µl per animal, of 30 mg/kg cortisone at 1 to 24 hours post compound dose. At 10 minutes post cortisone challenge, each animal is euthanized for 1 minute in a $CO_2$ chamber, followed by blood collection via cardiac puncture into serum separator tubes. Once fully clotted, tubes are spun at 2500×g, 4° C. for 15 minutes, the serum transferred to wells of 96-well plates (Corning Inc, Costar #4410, cluster tubes, 1.2 ml, polypropylene), and the plates are frozen at −20° C. until analysis by LC-MS/MS. For analysis, serum samples are thawed and the proteins are precipitated by the addition of acetonitrile containing d-4-corti-

| Example | Structure | $IC_{50}$ (nm) |
|---------|-----------|----------------|
| 5 | 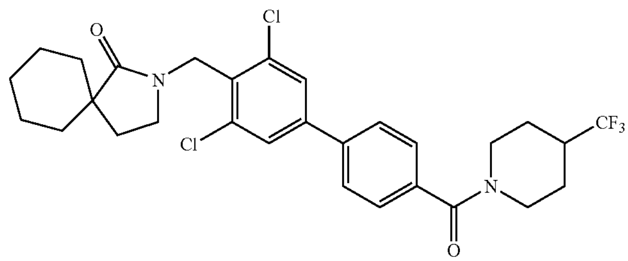 | 47 |
| 6 | 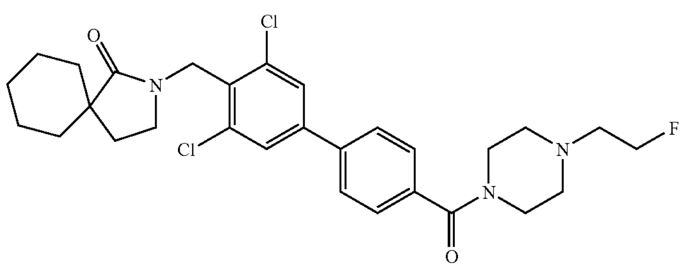 | 20.5 |
| 14 | 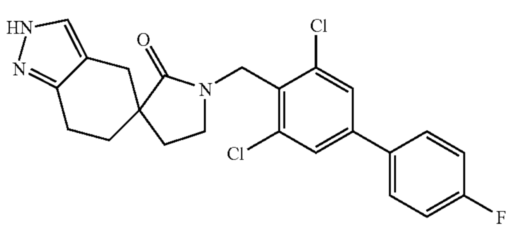 | 21.5 |

Acute In Vivo Cortisone Conversion Assay

In general, compounds are dosed orally into mice, the mice are challenged with a subcutaneous injection of cortisone at a set timepoint after compound injection, and the blood of each animal is collected some time later. Separated serum is then isolated and analyzed for levels of cortisone and cortisol by LC-MS/MS, followed by calculation of mean cortisol and percent inhibition of each dosing group. Specifically, male C57BL/6 mice are obtained from Harlan Sprague Dawley at sol internal standard. Samples are vortex mixed and centrifuged. The supernatant is removed and dried under a stream of warm nitrogen. Extracts are reconstituted in methanol/water (1:1) and injected onto the LC-MS/MS system. The levels of cortisone and cortisol are assayed by selective reaction monitoring mode following positive ACPI ionization on a triple quadrupole mass spectrophotometer.

Data for example compounds in the acute in vivo cortisone conversion assay are shown below:

| Example | Structure | % Inhibition after 16 hours (dose of 10 (mg/kg)) |
|---|---|---|
| 5 | 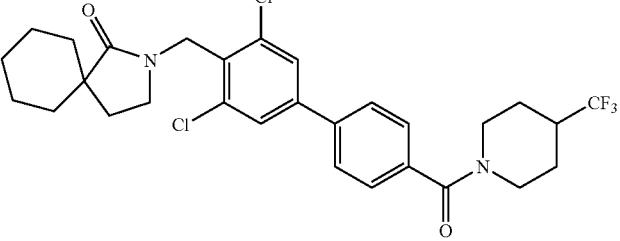 | 69.3 |
| 6 | 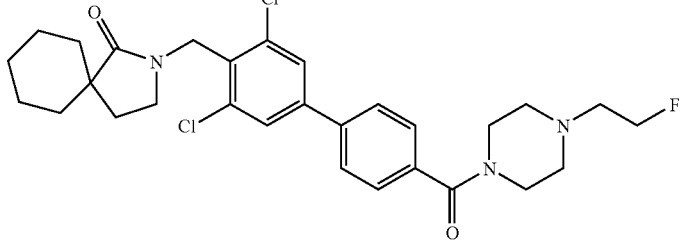 | 41.2 |

Pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977. The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (A. Gennaro, et al., eds., 19th ed., Mack Publishing Co., 1995).

The particular dosage of a compound of formula (I) or a pharmaceutically acceptable salt thereof required to constitute an effective amount according to this invention will depend upon the particular circumstances of the conditions to be treated. Considerations such as dosage, route of administration, and frequency of dosing are best decided by the attending physician. Generally, accepted and effective dose ranges for oral or parenteral administration will be from about 0.1 mg/kg/day to about 10 mg/kg/day which translates into about 6 mg to 600 mg, and more typically between 30 mg and 200 mg for human patients. Such dosages will be administered to a patient in need of treatment from one to three times each day or as often as needed to effectively treat a disease selected from those described herein.

One skilled in the art of preparing formulations can readily select the proper form and mode of administration depending upon the particular characteristics of the compound selected, the disorder or condition to be treated, the stage of the disorder or condition, and other relevant circumstances. (Remington's Pharmaceutical Sciences, 18th Edition, Mack Publishing Co. (1990)). The compounds claimed herein can be administered by a variety of routes. In effecting treatment of a patient afflicted with or at risk of developing the disorders described herein, a compound of formula (I) or a pharmaceutically acceptable salt thereof can be administered in any form or mode that makes the compound bioavailable in an effective amount, including oral and parenteral routes. For example, the active compounds can be administered rectally, orally, by inhalation, or by the subcutaneous, intramuscular, intravenous, transdermal, intranasal, rectal, ocular, topical, sublingual, buccal, or other routes. Oral administration may be preferred for treatment of the disorders described herein. In those instances where oral administration is impossible or not preferred, the composition may be made available in a form suitable for parenteral administration, e.g., intravenous, intraperitoneal or intramuscular.

What is claimed:
1. A compound structurally represented by the formula:

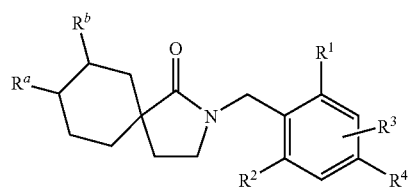

or a pharmaceutically acceptable salt thereof, wherein
$R^a$ is —H or —OH;
$R^b$ is —H; or
$R^a$ and $R^b$ combine with the cyclohexyl ring to which they are attached to form

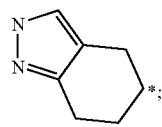

wherein the asterisk represents the carbon atom shared with the lactam ring;

$R^1$ is -halogen,
$R^1$ is -halogen,
$R^3$ is —H or -halogen;
$R^4$ is
—OH, -halogen, —CN, —(C$_1$-C$_4$)alkyl(optionally substituted with one to three halogens), —(C$_1$-C$_6$)alkoxy (optionally substituted with one to three halogens), —SCF$_3$, —C(O)O(C$_1$-C$_4$)alkyl, —O—CH$_2$—C(O)NH$_2$,
—(C$_3$-C$_8$)cycloalkyl, —O—phenyl—C(O)O—(C$_1$-C$_4$)alkyl, —CH$_2$-phenyl, —NHSO$_2$-(C$_1$-C$_4$)alkyl, —NHSO$_2$-phenyl(R$^{21}$)(R$^{21}$),
—(C$_1$-C$_4$)alkyl-C(O)N(R$^{10}$)(R$^{11}$),

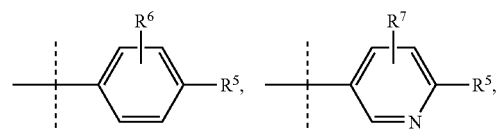

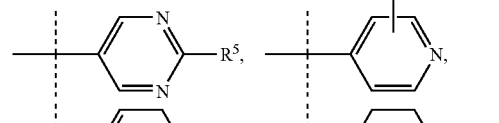

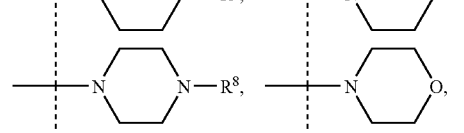

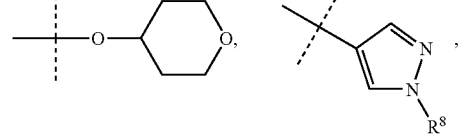

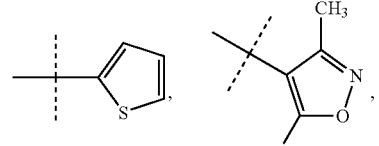

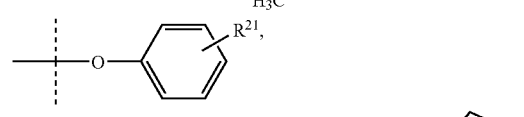

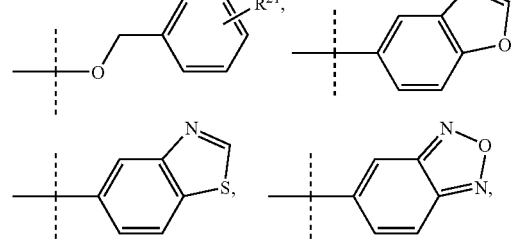

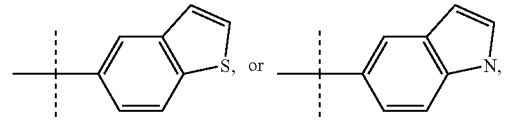

wherein the dashed line represents the point of attachment to the R$^4$ position;

$R^5$ is
—H, -halogen, —OH, —CN, —(C$_1$-C$_4$)alkyl(optionally substituted with 1 to 3 halogens), —C(O)OH, —C(O)O—(C$_1$-C$_4$)alkyl, —C(O)—(C$_1$-C$_4$)alkyl, —O—(C$_1$-C4)alkyl(optionally substituted with 1 to 3 halogens), —SO$_2$—(C$_1$-C1) alkyl, —N(R$^8$)(R$^8$), -phenyl(R$^{21}$)(R$^{21}$), —C(O)—NH—(C$_3$-C$_6$)cycloalkyl,

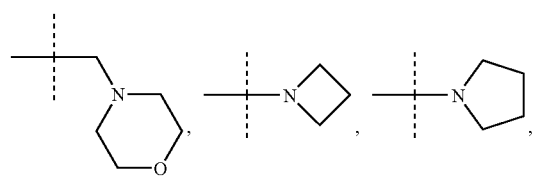

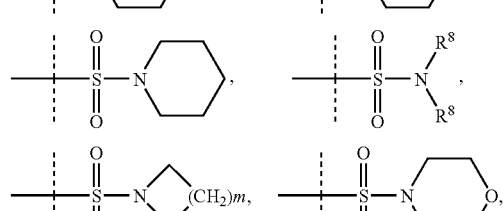

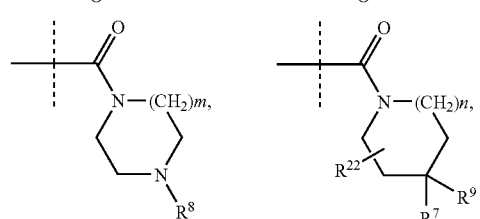

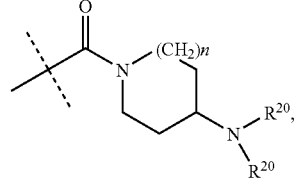

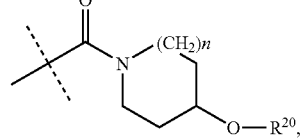

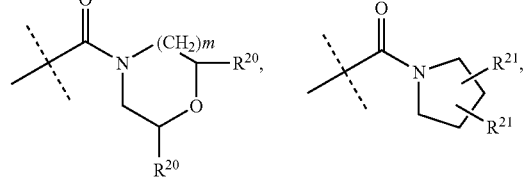

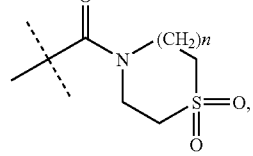

-continued

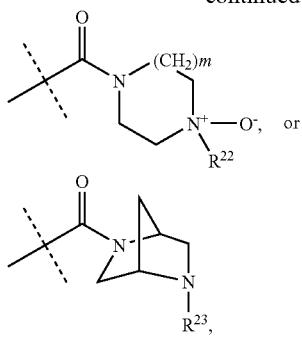

wherein the dashed line represents the point of attachment to the position indicated by $R^5$;

wherein m is 1, 2, or 3;

wherein n is 0, 1, or 2, and wherein when n is 0, then "(CH$_2$) n" is a bond;

$R^6$ is
—H, -halogen, —CN, or —(C$_1$-C$_4$)alkyl(optionally substituted with 1 to 3 halogens);

$R^7$ is
—H, -halogen, or —(C$_1$-C4)alkyl(optionally substituted with 1 to 3 halogens);

$R^8$ is independently at each occurrence —H or —(C$_1$-C$_6$) alkyl(optionally substituted with 1 to 3 halogens);

$R^9$ is —H or -halogen;

$R^{10}$ and $R^{11}$ are each independently
—H or —(C$_1$-C$_4$)alkyl, or $R^{10}$ and $R^{11}$ taken together with the nitrogen to which they are attached form piperidinyl, piperazinyl, or pyrrolidinyl;

$R^{20}$ is independently at each occurrence —H, or —(C$_1$-C$_3$) alkyl(optionally substituted with 1 to 3 halogens);

$R^{21}$ is independently at each occurrence —H, -halogen, or —(C$_1$-C$_3$)alkyl(optionally substituted with 1 to 3 halogens);

$R^{22}$ is independently at each occurrence —H or —(C$_1$-C$_6$) alkyl(optionally substituted with 1 to 3 halogens); and $R^{23}$ is independently at each occurrence —H, —(C$_1$-C$_4$) alkyl(optionally substituted with 1 to 3 halogens), or —C(O)O—(C$_1$-C$_4$)alkyl.

2. A compound of claim 1 wherein $R^a$ and $R^b$ are hydrogen, or a pharmaceutically acceptable salt thereof.

3. A compound of claim 1 wherein $R^a$ is —OH and $R^b$ is hydrogen, or a pharmaceutically acceptable salt thereof.

4. A compound of claim 1 wherein $R^a$ and $R^b$ combine with the cyclohexyl ring to which they are attached to form

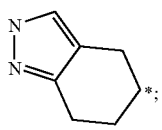

wherein the asterisk represents the carbon atom shared with the lactam ring, or a pharmaceutically acceptable salt thereof.

5. A compound of claim 1 wherein $R^1$ is -chlorine and $R^2$ is -chlorine, and $R^3$ is —H, or a pharmaceutically acceptable salt thereof.

6. A compound of claim 5, wherein $R^4$ is

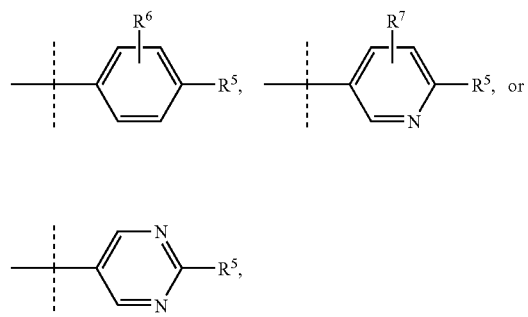

or a pharmaceutically acceptable salt thereof.

7. A compound of claim 5, wherein $R^4$ is

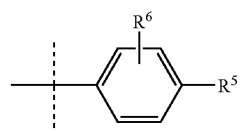

and $R^6$ is —H, or a pharmaceutically acceptable salt thereof.

8. A compound of claim 7 wherein $R^5$ is

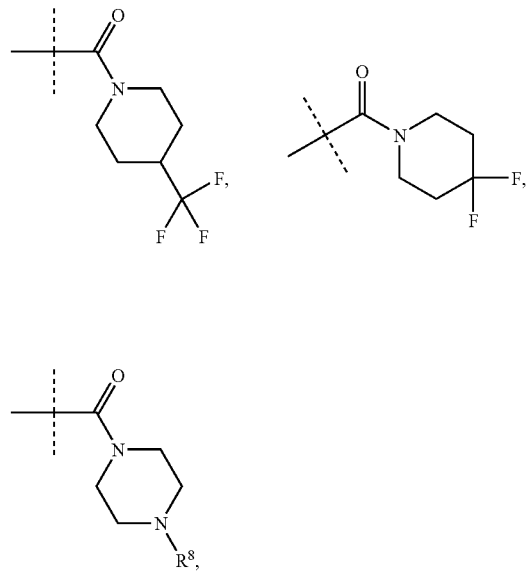

wherein $R^8$ is —(C$_1$-C$_3$)alkyl (optionally substituted with 1 to 3 halogens), or

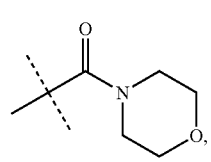

or a pharmaceutically acceptable salt thereof.

9. A compound of claim 7 wherein $R^5$ is

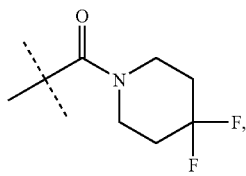

or a pharmaceutically acceptable salt thereof,

10. A compound of claim 7 wherein $R^5$ is

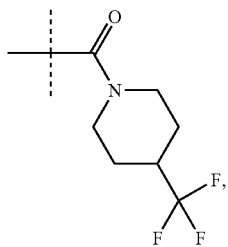

or a pharmaceutically acceptable salt thereof.

11. A compound of claim 7, wherein $R^5$ is

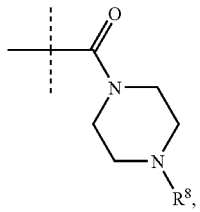

wherein $R^8$ is —($C_1$-$C_3$)alkyl (optionally substituted with 1 to 3 halogens), or a pharmaceutically acceptable salt thereof.

12. A compound of claim 7 wherein $R^5$ is chlorine or fluorine, or a pharmaceutically acceptable salt thereof.

13. A compound that is 2-[3,5-Dichloro-4'(4-trifluoromethyl-piperidine- 1-carbonyl)-biphenyl-4-ylmethyl]-2-aza-spiro[4.5]decan-1-one or a pharmaceutically acceptable salt thereof.

14. A compound that is 2- (3,5-Dichloro-4'-[4-(2-fluoro-ethyl)-piperazine-1-carbonyl]-biphenyl-4-ylmethyl)-2-aza-spiro[4.5]decan-1-one or a pharmaceutically acceptable salt thereof.

15. A pharmaceutical composition which comprises a compound of claim 1, or a stereoisomer thereof, or a pharmaceutically acceptable salt thereof, and a pharmaceutically acceptable carrier.

16. A method for treating type 2 diabetes in a patient in need thereof which comprises administering to said patient an effective amount of a compound of claim 1, or a pharmaceutically acceptable salt thereof.

17. An intermediate for preparing a compound of claim 13 wherein the intermediate is

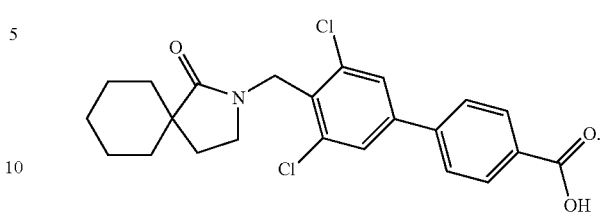

18. A compound of claim 1 selected from the group consisting of:
2-(4-Bromo-2,6-dichloro-benzyl)-2-aza-spiro[4.5]decan-1-one;
2-(3,5-Dichloro-4'-fluoro-biphenyl-4-ylmethyl)-2-aza-spiro[4.5]decan-1-one;
3',5'-Dichloro-4'-(1-oxo-2-aza-spiro[4.5]dec-2-ylmethyl)-biphenyl-4-carboxylic acid methyl ester;
3',5'-Dichloro-4'-(1-oxo-2-aza-spiro[4.5]dec-2-ylmethyl)-biphenyl-4-carboxylic acid;
2- [3,5-Dichloro-4'-(4-trifluoromethyl-piperidine-1-carbonyl)-biphenyl-4-ylmethyl]-2-aza-spiro [4.5]decan-1-one;
2- (3,5-Dichloro-4'[4-(2-fluoro-ethyl)-piperazine-1-carbonyl)-biphenyl-4-ylmethyl]-2-aza-spiro [4.5]decan-1-one;
2-(2,6-Dichloro-4-morpholin-4-yl-benzyl)-2-aza-spiro[4.5]decan-1-one;
trans 2-[3,5-Dichloro-4'-(4-trifluoromethyl-piperidine-1-carbonyl)-biphenyl-4-ylmethyl]-8-hydroxy-2-aza-spiro[4.5]decan-1-one;
cis2-[3,5-Dichloro-4'-4-trifluoromethyl-piperidine-1-carbonyl]-biphenyl-4-ylmethyl]-8-hydroxy-2-aza-spiro [4.5]decan-1-one;
cis-[3,5-Dichloro-4'-(4,4-difluoro-piperidine-1-carbonyl)-biphenyl-4-ylmethyl]-8-hydroxy-2-aza-spiro[4,5]decan-1-one;
trans-[3,5-Dichloro-4'(4,4-difluoro-piperidine-1-carbonyl)-biphenyl-4-ylmethyl]-8-hydroxy-2-aza-spiro[4.5]decan-1-one;
cis2-(3,5-Dichloro4'-fluoro-biphenyl-4-ylmethyl)-8-hydroxy-2-aza-spiro[4.5]decan-1-one;

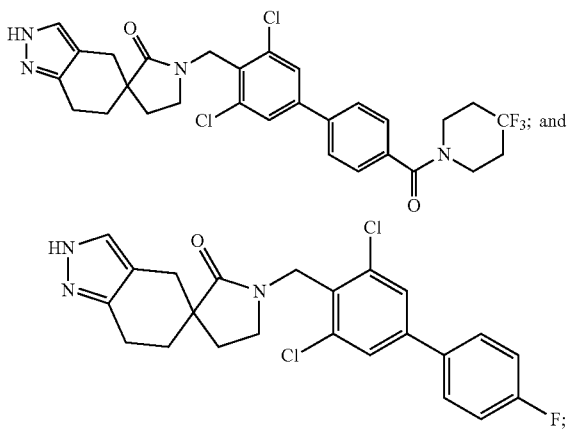

or a pharmaceutically acceptable salt thereof.

* * * * *